(12) United States Patent
Schuele et al.

(10) Patent No.: US 9,078,679 B2
(45) Date of Patent: Jul. 14, 2015

(54) METHOD AND APPARATUS FOR A RADIOLUCENT AND MRI COMPATIBLE CRANIAL STABILIZATION PIN

(75) Inventors: Matthias E. Schuele, Freiburg (DE); Edgar F. Schuele, Freiburg (DE); Matthias E. Schuele, legal representative, Freiburg (DE); Christian P. Schuele, legal representative, Freiburg (DE); Thomas C. Schuele, legal representative, Munich (DE)

(73) Assignee: pro med instruments GmbH, Freiburg (DE)

( * ) Notice: Subject to any disclaimer, the term of this patent is extended or adjusted under 35 U.S.C. 154(b) by 1341 days.

(21) Appl. No.: 12/712,716

(22) Filed: Feb. 25, 2010

(65) Prior Publication Data
US 2010/0217280 A1 Aug. 26, 2010

Related U.S. Application Data

(60) Provisional application No. 61/155,701, filed on Feb. 26, 2009.

(51) Int. Cl.
*A61B 17/04* (2006.01)
*A61B 17/84* (2006.01)
*A61B 17/86* (2006.01)
*A61F 2/08* (2006.01)
(Continued)

(52) U.S. Cl.
CPC ....... *A61B 19/203* (2013.01); *A61B 2017/0092* (2013.01); *A61B 2017/00911* (2013.01); *A61B 2017/00915* (2013.01)

(58) Field of Classification Search
USPC .......................................... 606/329
See application file for complete search history.

(56) References Cited

U.S. PATENT DOCUMENTS 3,835,861 A  9/1974  Kees et al.
4,169,478 A  10/1979 Hickmann
(Continued)

FOREIGN PATENT DOCUMENTS

EP  1 026 513  8/2000
EP  2 014 251  1/2009
(Continued)

OTHER PUBLICATIONS

International Search Report dated Oct. 18, 2010 for Application No. PCT/IB2010/000513.
(Continued)

*Primary Examiner* — Sameh Boles
(74) *Attorney, Agent, or Firm* — Frost Brown Todd LLC

(57) ABSTRACT

A substantially radiolucent cranial stabilization pin is adapted for use with a fixture for immobilizing a patient's head during a medical procedure. The pin includes a tip and a body, which are secured together to form the pin. The tip and body are constructed from non-ferrous, non-magnetic materials that are biocompatible. The tip and body are safe for use with, and compatible with, imaging techniques including MR imaging and CT imaging. In some examples the tip is a titanium insert and the body is molded within and around at least a portion of the tip. In some versions, the tip includes a hollow portion and one or more openings providing access to the hollow portion. The molded body flows into and around portions of the tip creating a secure pin suitable to withstand torque and axial forces observed in use.

7 Claims, 28 Drawing Sheets

(51) Int. Cl.
*A61B 19/00* (2006.01)
*A61B 17/00* (2006.01)

(56) References Cited

U.S. PATENT DOCUMENTS

| | | | |
|---|---|---|---|
| 4,392,645 A | 7/1983 | Westphal |
| 4,397,307 A | 8/1983 | Keller |
| 4,444,179 A | 4/1984 | Trippi |
| 4,475,550 A | 10/1984 | Bremer et al. |
| 4,539,979 A | 9/1985 | Bremer |
| 4,541,421 A | 9/1985 | Iversen et al. |
| 4,612,930 A | 9/1986 | Bremer |
| 4,796,846 A | 1/1989 | Meier et al. |
| 4,838,264 A | 6/1989 | Bremer et al. |
| 5,042,462 A | 8/1991 | Bremer |
| 5,062,415 A | 11/1991 | Weatherby et al. |
| 5,122,132 A | 6/1992 | Bremer |
| 5,156,588 A | 10/1992 | Marcune et al. |
| 5,180,361 A | 1/1993 | Moore et al. |
| 5,197,965 A | 3/1993 | Cherry et al. |
| 5,254,079 A | 10/1993 | Agbodoe et al. |
| 5,276,927 A | 1/1994 | Day |
| 5,300,076 A | 4/1994 | Leriche |
| 5,302,170 A | 4/1994 | Tweardy |
| 5,318,509 A | 6/1994 | Agbodoe |
| 5,347,894 A | 9/1994 | Fischer |
| 5,437,612 A | 8/1995 | Moore et al. |
| 5,537,704 A | 7/1996 | Dinkler et al. |
| 5,549,620 A | 8/1996 | Bremer |
| 5,632,722 A | 5/1997 | Tweardy et al. |
| 5,643,268 A | 7/1997 | Vilsmeier et al. |
| 5,961,528 A | 10/1999 | Birk et al. |
| 6,045,553 A | 4/2000 | Iversen et al. |
| 6,306,146 B1 | 10/2001 | Dinkler |
| 6,379,362 B1 | 4/2002 | Birk et al. |
| 6,598,275 B1 | 7/2003 | Kolody et al. |
| 6,635,064 B2 | 10/2003 | U et al. |
| 6,684,428 B2 | 2/2004 | Grotenhuis et al. |
| 6,896,678 B2 | 5/2005 | Tweardy |
| 7,011,619 B1 | 3/2006 | Lewis et al. |
| 7,048,735 B2 | 5/2006 | Ferrante et al. |
| 7,246,975 B2 | 7/2007 | Corso et al. |
| 7,507,244 B2 | 3/2009 | Dinkler |
| 7,905,884 B2 | 3/2011 | Simonton et al. |
| 8,104,477 B2 | 1/2012 | Edlauer et al. |
| 2006/0084900 A1 | 4/2006 | Schüle |
| 2007/0270801 A1* | 11/2007 | Arn et al. ............... 606/54 |
| 2008/0251086 A1 | 10/2008 | Dinkler |
| 2009/0264938 A1 | 10/2009 | Bailey et al. |
| 2010/0059064 A1 | 3/2010 | Schüle et al. |
| 2011/0257689 A1* | 10/2011 | Fiechter et al. ........ 606/301 |

FOREIGN PATENT DOCUMENTS

| WO | WO 97/40764 | 4/1997 |
|---|---|---|
| WO | WO 02/085187 | 10/2002 |

OTHER PUBLICATIONS

International Preliminary Report on Patentability dated Aug. 30, 2011 for Application No. PCT/IB2010/000513.
Notification Concerning Transmittal of International Preliminary Report on Patentability (Chapter 1 of the Patent Cooperation Treaty) dated Sep. 9, 2011 for Application No. PCT/IB2010/000513.
EPO Search Report dated May 11, 2006 for Application No. EP 05292169.
"Accessories" Officine Sordina S.p.A.
"Bookwalter Retractor Kit II," Codman.
Doro® Skull Pins, pro med instruments, Inc., available at http://www.headrest.de/contentcenter/daten/files/Skull_Pins_Flyer_V01.pdf.
Screenshots from www.integra-ls.com, printed Dec. 8, 2005.
Screenshots from www.integra-ls.com, printed Jan. 28, 2005.
Screenshots of Surgical Tables Accessories from www.bicakcilar.com, printed Jan. 28, 2005.

* cited by examiner

METHOD AND APPARATUS FOR A RADIOLUCENT AND MRI COMPATIBLE CRANIAL STABILIZATION PIN

PRIORITY

This application claims priority from the disclosure of U.S. Provisional Patent Application Ser. No. 61/155,701, entitled "METHOD AND APPARATUS FOR A RADIOLUCENT CRANIAL STABILIZATION PIN," filed Feb. 26, 2009, the disclosure of which is incorporated by reference herein.

BACKGROUND

During some surgical operations or other procedures, a portion of the body upon which surgery is being conducted may be substantially immobilized, such as, for example, a patient's head during head or neck surgery. Such immobilization of a patient's head, for example, may be accomplished with a fixture such as a skull clamp or other fixture, as disclosed in U.S. Patent Publication No. 2006/0084900, entitled METHOD AND APPARATUS FOR ATTACHING ACCESSORIES TO A SURGICAL FIXTURE, published Apr. 20, 2006, and in U.S. patent application Ser. No. 12/437,227, METHOD AND APPARATUS FOR USING A SURGICAL FIXTURE IN AN INTRA-OPERATIVE COMPUTED TOMOGRAPHY SCANNER, filed May 7, 2009, the disclosures of which are incorporated by reference herein. Other examples of cranial stabilization systems and components include any of the DORO products of pro med instruments GmbH of Freiburg, Germany. These and other devices may be used with cranial stabilization pins, also referred to as skull pins, which may be used to securely hold a patient's head within the skull clamp or other device.

It may be desirable to use such a cranial immobilization system or technique with a surgical procedure using intra-operative computed tomography (CT) scanning or other types of imaging (e.g., MRI, PEM, X-Ray, etc.). In some circumstances, it may be desirable and convenient for components of the cranial immobilization system to be compatible with the imaging technology, e.g. MRI, and further radiolucent. For example, it may be desirable that the skull pins be substantially or completely radiolucent and safe for use with MRI, yet still provide sufficient durability in use. While many surgical accessories and immobilization fixtures exist, it is believed that no one prior to the inventors has created or used the invention described herein.

BRIEF DESCRIPTION OF THE DRAWINGS

The accompanying drawings incorporated in and forming a part of the specification illustrate several aspects of the present invention, and together with the description serve to explain the principles of the invention; it being understood, however, that this invention is not limited to the precise arrangements shown. In the drawings, like reference numerals refer to like elements in the several views. In the drawings.

DETAILED DESCRIPTION

Figure 1:
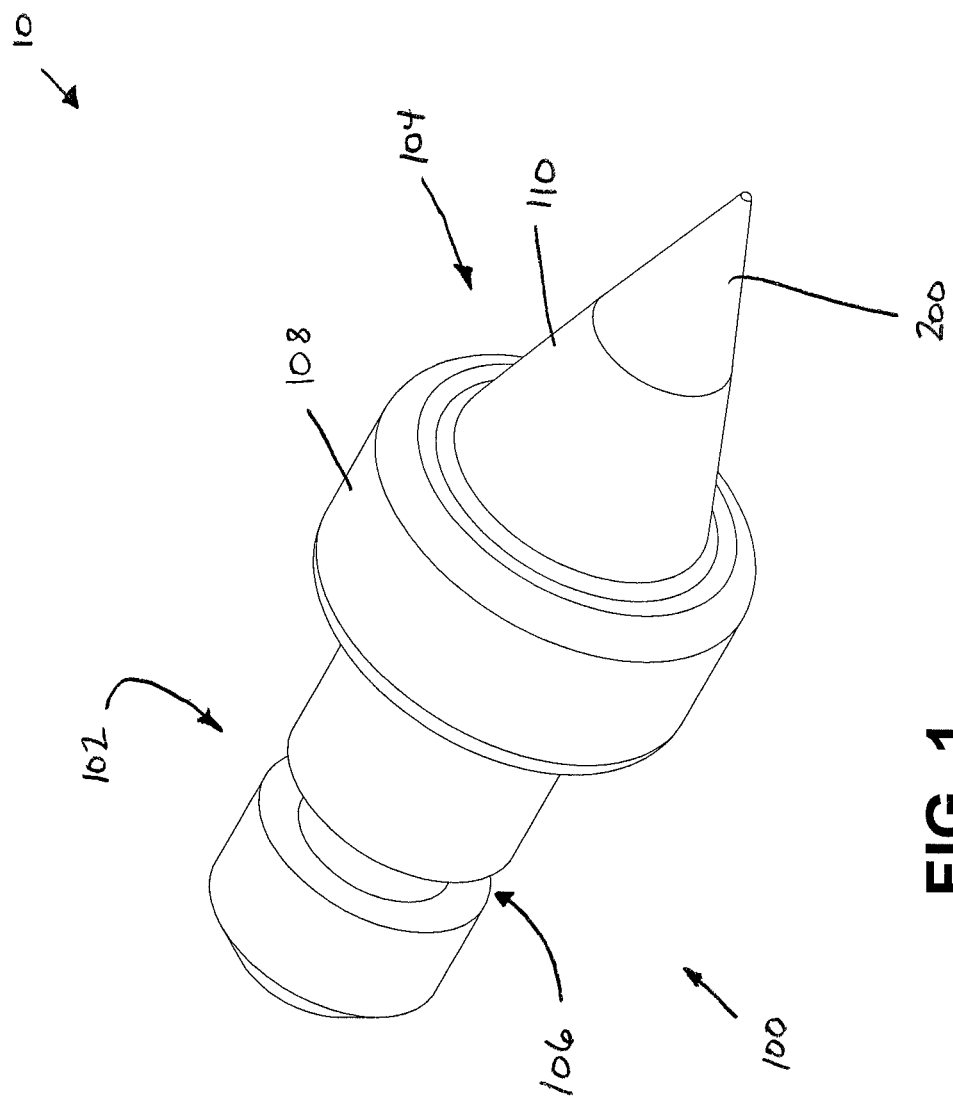
FIG. 1 depicts a perspective view of an exemplary cranial stabilization pin.

The following description of certain examples of the invention should not be used to limit the scope of the present invention. Other examples, features, aspects, versions, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the descriptions should be regarded as illustrative in nature and not restrictive.

FIGS. 1-24 depict various views of exemplary cranial stabilization pins, or components thereof, configured for use in a cranial immobilization fixture as referenced and described above. Such cranial stabilization pins are sometimes referred to as skull pins, or pins. The pins are configured to be safe for use with and compatible with imaging techniques including x-ray, computed tomography (CT) and magnetic resonance (MR). The pins are at least partially radiolucent and are configured to produce only a minimal artifact in the output of an imaging scan. The pins are constructed such that they can withstand the torque and axial forces typical in a skull stabilization procedure.

Referring to FIGS. 1-6, an exemplary version of cranial stabilization pin (10) is shown. Pin (10) comprises a body (100) and tip (200). Body (100) comprises proximal end (102) and distal end (104). Proximal end (102) is configured for secure attachment with a pin-holding component of a skull clamp or other device, e.g. a skull clamp as described in U.S. Patent Publication No. 2006/0084900, entitled METHOD AND APPARATUS FOR ATTACHING ACCESSORIES TO A SURGICAL FIXTURE, published Apr. 20, 2006, or in U.S. patent application Ser. No. 12/437,227, METHOD AND APPARATUS FOR USING A SURGICAL FIXTURE IN AN INTRA-OPERATIVE COMPUTED TOMOGRAPHY SCANNER, filed May 7, 2009, the disclosures of which are incorporated by reference herein. By way of example, proximal end (102) has a generally cylindrical shape that is configured to fit within a matching bore of a pin-holding component of a skull clamp. In the example shown in FIG. 1, proximal end (102) includes an annular recess (106). Annular recess (106) allows for a pin-holding component of a skull clamp to grip proximal end (102) of pin (10). Annular recess (106) may also be fitted with an o-ring (not shown) to assist in securing to the pin-holding component of a skull clamp or other device. In some other versions, proximal end (102) lacks annular recess (106). Other suitable features and configurations that may be provided at proximal end (102) such that pin (10) can be associated with a pin-holding component of a skull clamp or other device will be apparent to those of ordinary skill in the art in view of the teachings herein.

Distal end (104) of pin (10) of the present example comprises annular collar (108) and a conical protrusion (110). Annular collar (108) provides first surface (112) that is configured to act as a stop by contacting a portion of a pin-holding component of a skull clamp or other device. Conical protrusion (110) extends distally from body (100), tapering from larger to smaller diameter as protrusion (110) extends distally. At a distal-most end, conical protrusion (110) is associated with tip (200). Of course, distal end (104) of pin (10) may have a variety of other types of features and configurations in addition to or in lieu of having annular collar (108) and/or conical protrusion (110).

Figure 4:
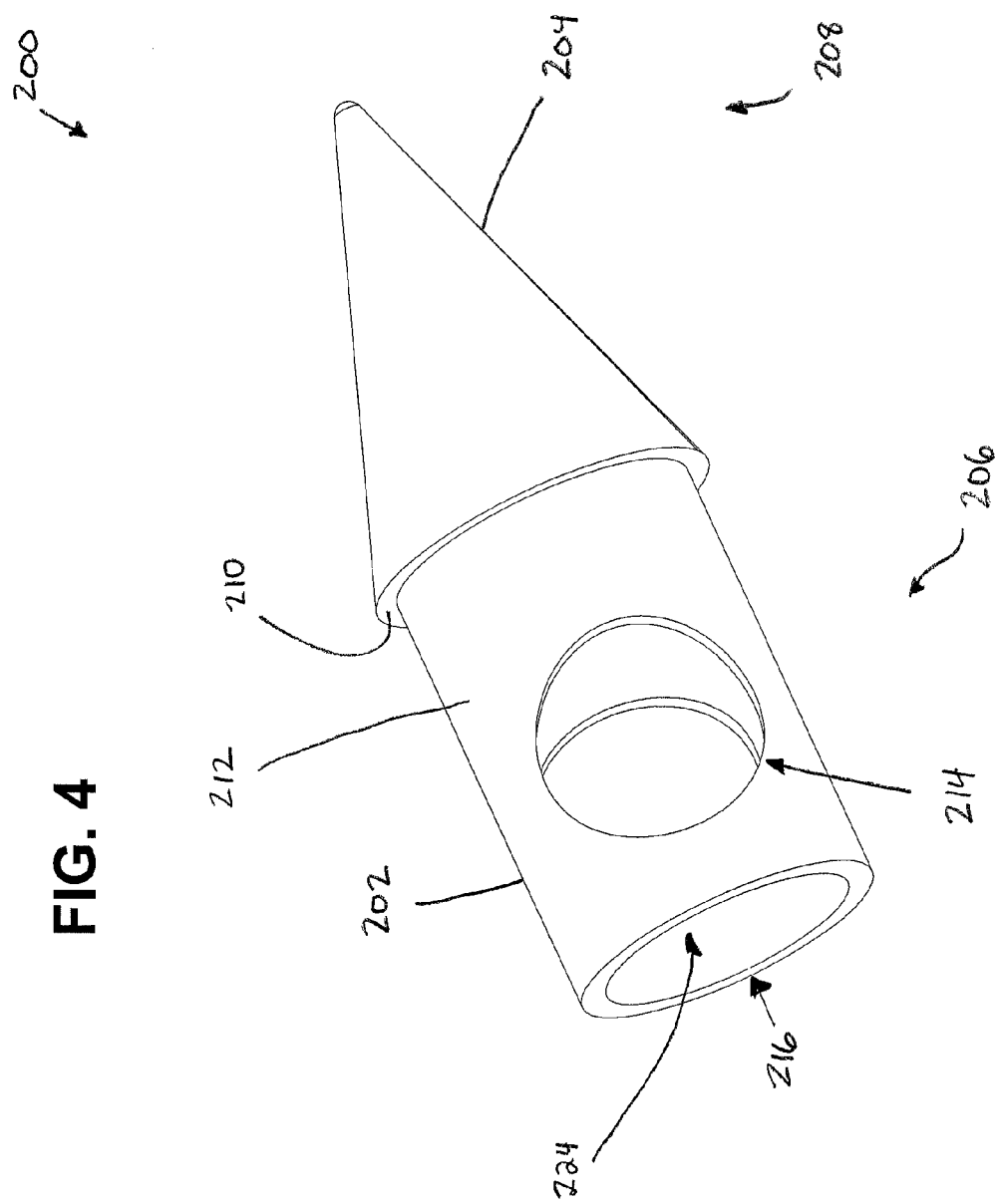
FIG. 4 depicts a perspective view of the tip of the pin of FIG. 1.

Tip (200) is largely a hollow structure comprising shaft (202) and conical protrusion (204). Shaft (202) is located along proximal end (206) of tip (200), and conical protrusion (204) is located along distal end (208) of tip (200). Conical protrusion (204) extends distally from shaft (202), tapering to a point at its distal-most end. At its proximal-most end, conical protrusion (204) includes lip (210). Lip (210) has a diameter greater than shaft (202) such that lip (210) overhangs shaft (202). Shaft (202) comprises sidewall (212), and sidewall (212) is configured with one or more openings (214). For example, as shown in FIG. 4, sidewall (212) includes two circular-shaped openings (214). Shaft (202) also comprises open end (216), which provides access to void space (224) within tip (200).

Figure 5:
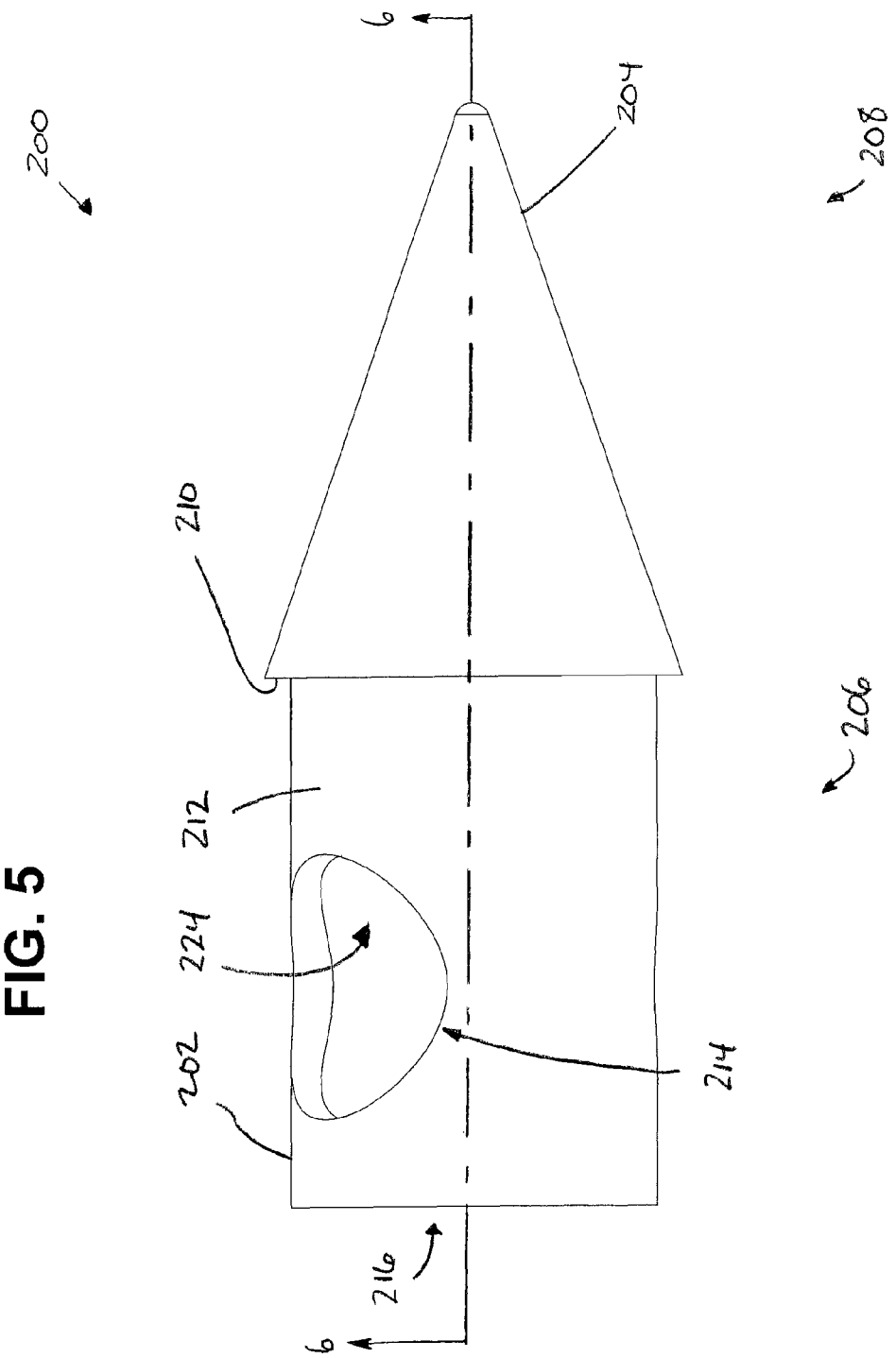
FIG. 5 depicts a side view of the tip of FIG. 4.

In some versions, tip (200) is constructed from a non-magnetic metal, such as titanium. During fabrication, a solid piece of titanium is milled and/or turned to create the general shape as shown in FIGS. 4 and 5. After milling and/or turning, the shaped titanium piece is drilled to incorporate openings (214) in sidewall (212). An additional drilling act is then used to hollow-out tip (200) by drilling along the longitudinal axis of tip (200) to create open end (216) and void space (224). Based on the teachings herein, other ways to fabricate tip (200) and other materials suitable for tip (200) will be apparent to those of ordinary skill in the art. By way of example only, other suitable materials to fabric the tips disclosed herein may include ceramics, other non-magnetic metals, glass-fiber reinforced materials, carbon-fiber reinforced materials, among others.

Figure 2:
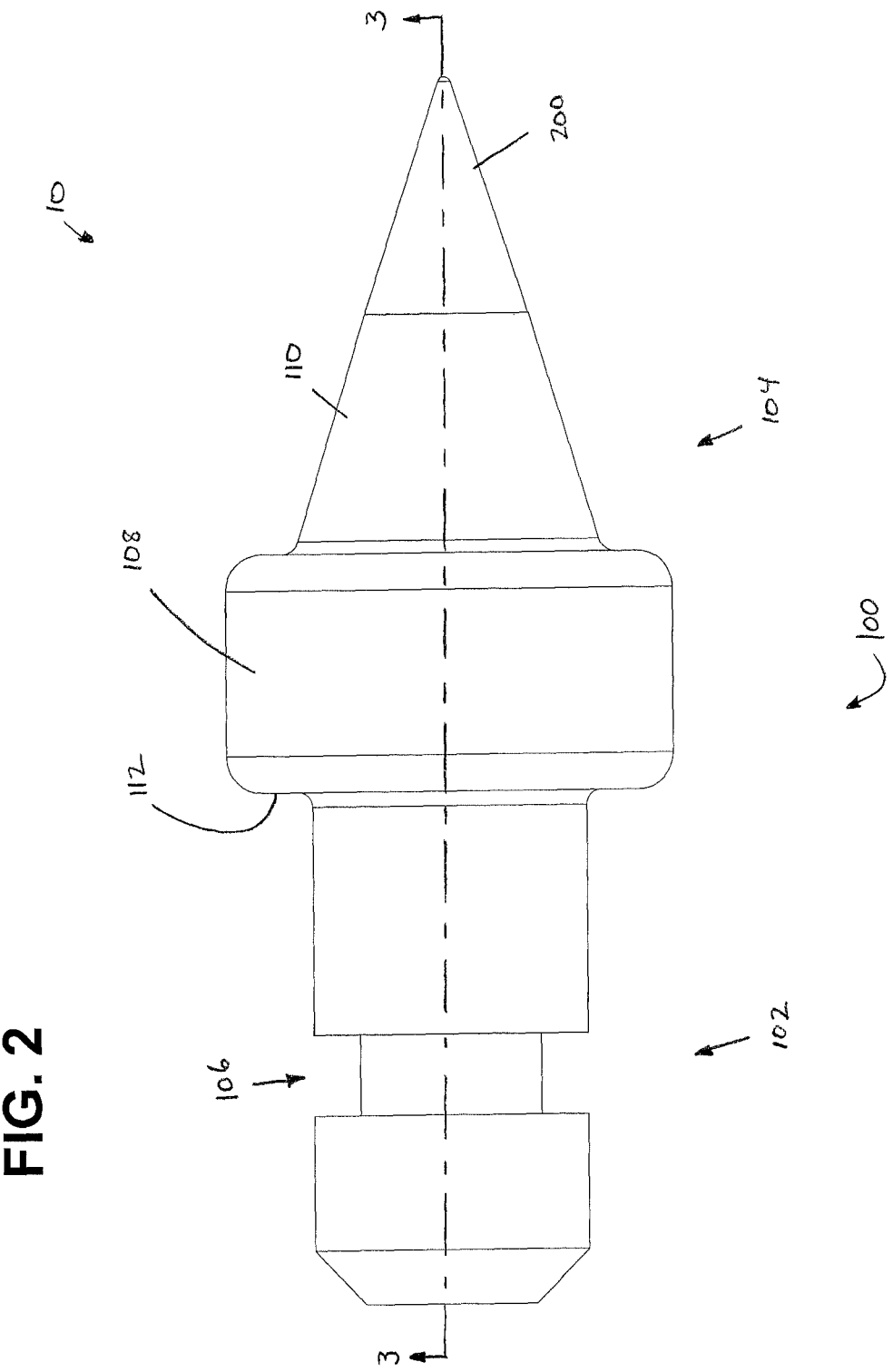
FIG. 2 depicts a side view of the pin of FIG. 1.

In some versions, body (100) is constructed from a plastic by an injection molding process. Suitable plastics may include polyether-etherketone (PEEK), duroplastic, and/or other thermoplastics or thermosetting plastics, all or any of which may include glass-fiber and/or carbon-fiber reinforcement. Moreover, in some versions, body (100) and tip (200) are securely joined via the injection molding process. For example, tip (200) is positioned within the injection mold as an insert, and body (100) is molded around and within tip (200). Where such a process is used, the molten plastic flows into void space (224) of tip (200) via open end (216) of shaft (202) and openings (214) in sidewall (212). The molten plastic fills void space (224) within tip (200) and overflows to encapsulate shaft (202). The shape of the mold is such that the molten plastic continues to form body (100) in the shape as shown in FIGS. 1-2.

Figure 3:
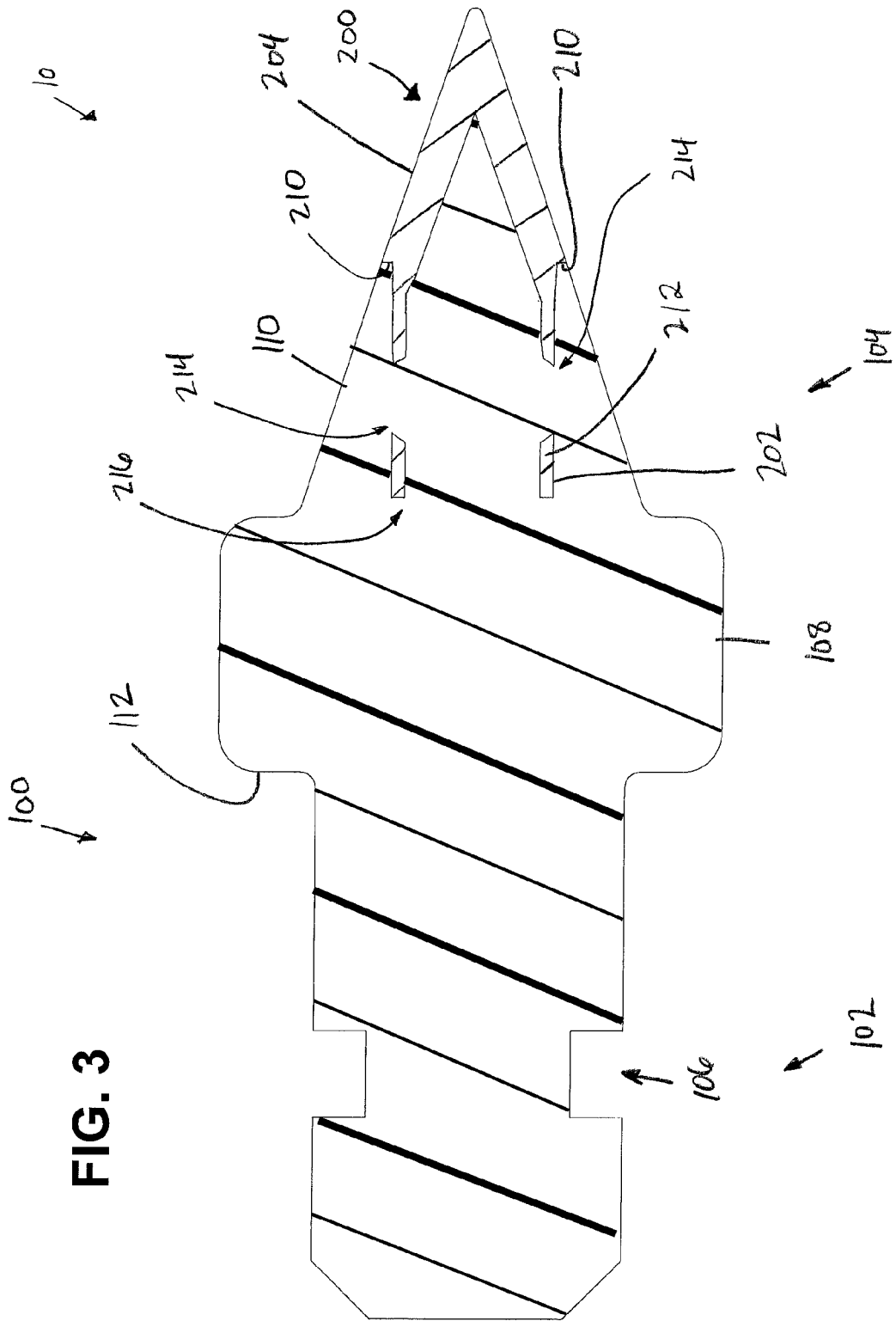
FIG. 3 depicts a cross section view of the pin of FIG. 2, taken along line 3-3 of FIG. 2.
Figure 6:
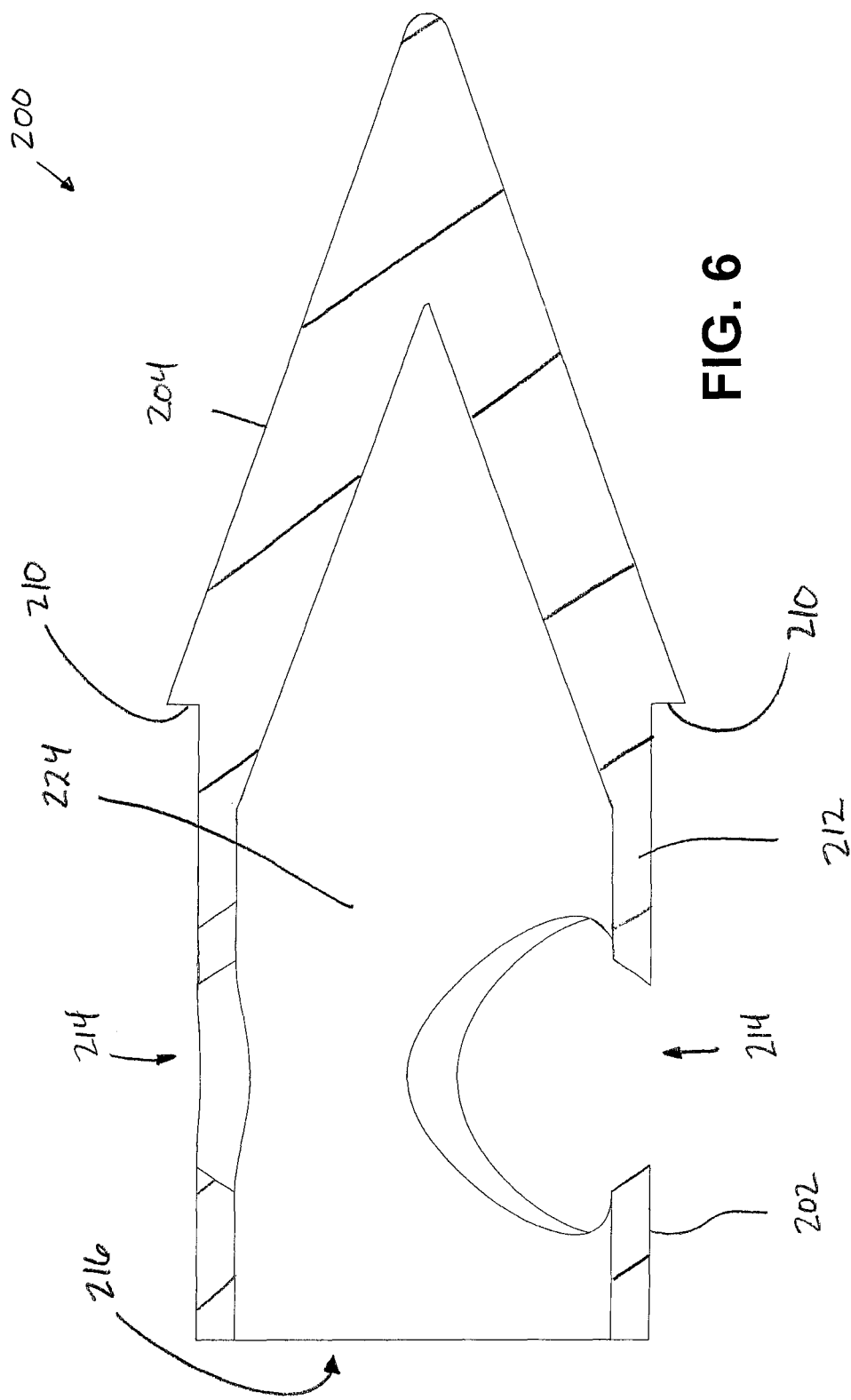
FIG. 6 depicts a cross section view of the tip of FIG. 5, taken along the line 6-6 of FIG. 5.

Referring to FIGS. 3 and 6, cross sections of pin (10) and tip (200) show that final pin (10), in an injection molded design, has the plastic of body (100) encompassing void space (224) of tip (200) and surrounding proximal end (206) of tip (200) where shaft (202) is located. Also, lip (210) of tip (200) abuts conical protrusion (110) of body (100) to provide a smooth transition from tip (200) to body (100). Using such a design and fabrication process, pin (10) is safe for use with and compatible with MR imaging, and pin (10) is substantially radiolucent with a strong tip (200) having low mass such that only a minimal artifact is seen in the output of an imaging scan. Furthermore, using such a design and fabrication process, tip (200) and body (100) are securely joined such that pin (10) can withstand the torque and axial forces typical in a skull stabilization procedure using a skull clamp or other device. For instance, molding body (100) to tip (200) by molding plastic not only around the exterior surface of a portion of a low mass tip (200), but also within and through portions of tip (200) provides as strong and secure connection between body (100) and tip (200), suitable for withstanding torque and axial forces experienced in use.

While body (100) has been described as being constructed of plastic, and by an injection molding process, other suitable materials and methods of construction will be apparent to those of ordinary skill in the art in view the teachings herein. For example, body (100) may be fabricated by machining by turning, milling, etc. instead of injection molding. Additionally, based on the teachings herein, other ways to securely join tip (200) and body (100) will be apparent to those of ordinary skill in the art. For example, tip (200) and body (100) may be securely joined with an adhesive.

Referring to FIGS. 7-10, another exemplary pin (20) is shown. Pin (20) generally has the same or similar appearance as pin (10), as shown in FIGS. 1-2. In fact, pin (20) is identical to pin (10) with the exception that pin (20) comprises a different tip. Thus the functionality of pin (20) is the same or similar to pin (10) and the preceding paragraphs describing the functionality of pin (10) apply equally to pin (20).

Pin (20) comprises body (300) and tip (400). Tip (400) is largely a hollow structure comprising shaft (402), conical protrusion (404), and collar (405). Collar (405) is located along proximal end (406) of tip (400), and conical protrusion (404) is located along distal end (408) of tip (400). Shaft (402) extends between collar (405) and conical protrusion (404). Conical protrusion (404) extends distally from shaft (402), tapering to a point at its distal-most end. At its proximal-most end, conical protrusion (404) includes lip (410). Lip (410) has a diameter greater than shaft (402) such that lip (410) overhangs shaft (402). As shown in FIGS. 7-10, shaft (402) comprises sidewall (412) that is without openings as described above with respect to pin (10). Of course, in some versions openings similar to that shown with pin (10) may be incorporated into sidewall (412) of shaft (402). Shaft (402) extends proximally from lip (410) of conical protrusion (404) and terminates with its connection to collar (405). In the present example, collar (405) comprises a general u-shape, having circular flange portion (418) with first and second fins (420, 422) extending proximally from flange portion (418). Collar (405) also comprises open end (416) in the center of flange portion (418), which provides access to void space (424) within tip (400). Of course, in some versions collar (405) may have shapes other than a u-shape, e.g. a circular shape the same as or similar to that shown in FIG. 24.

Figure 8:
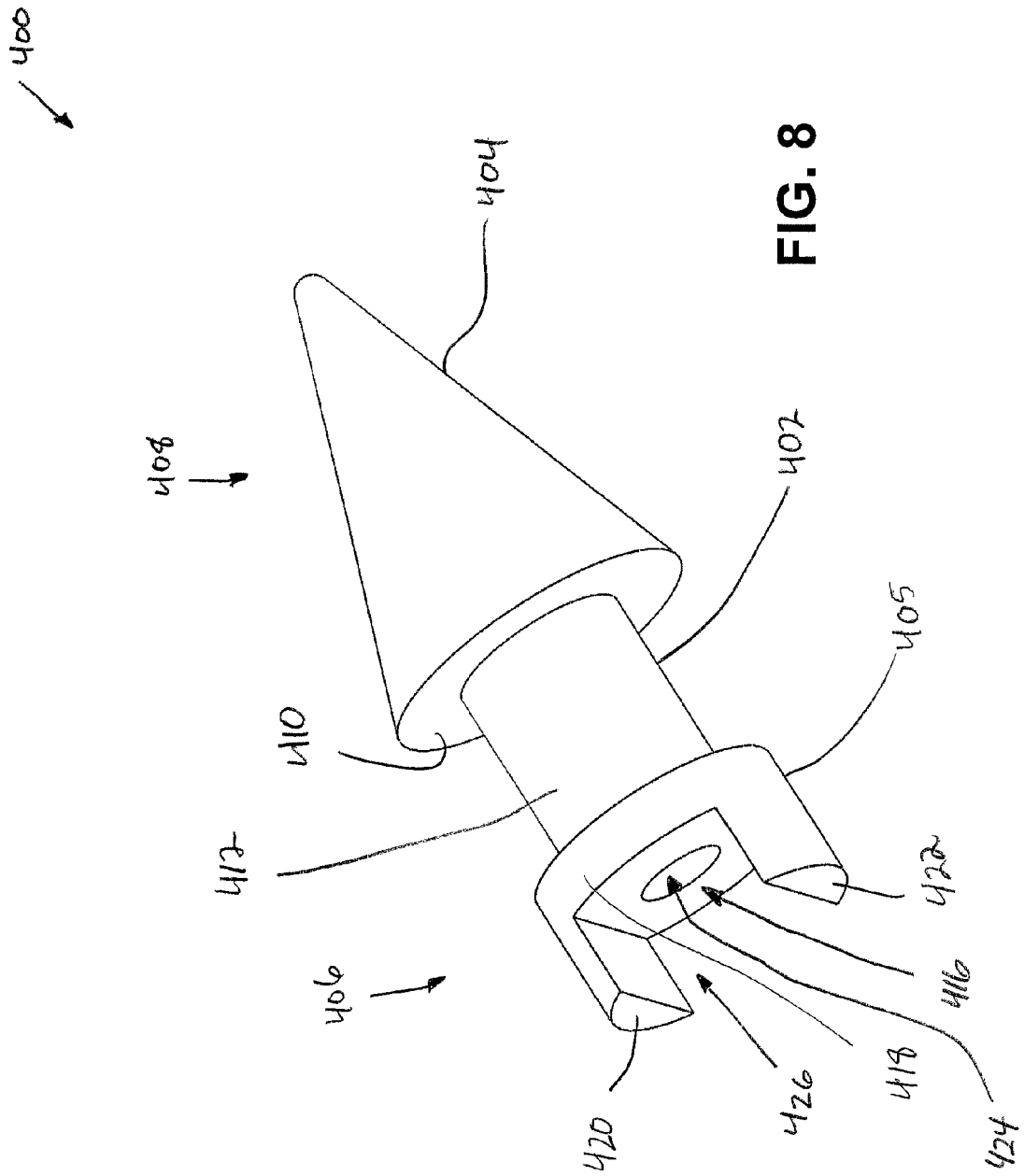
FIG. 8 depicts a perspective view of the tip of the pin of FIG. 7.
Figure 9:
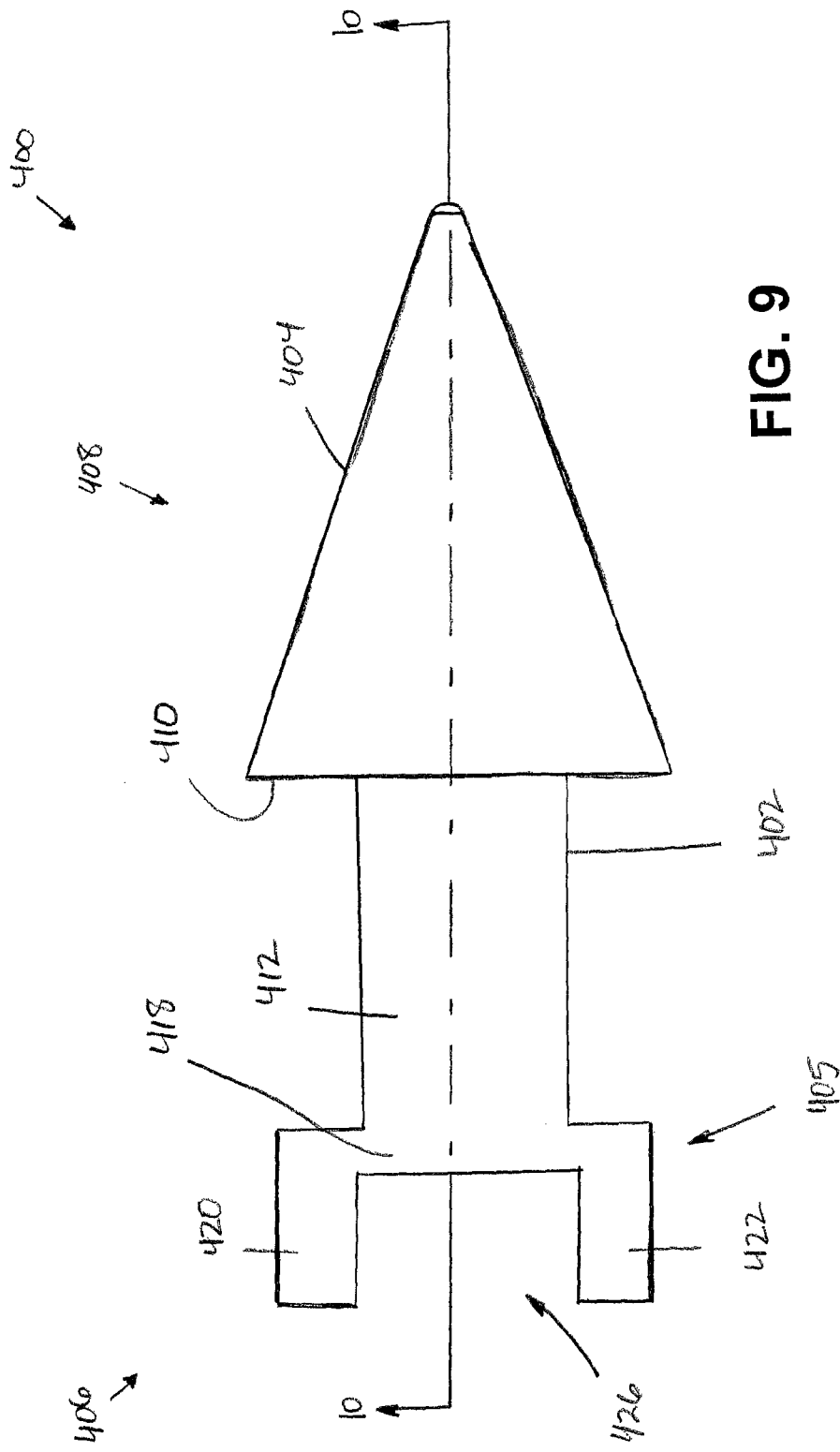
FIG. 9 depicts a side view of the tip of FIG. 8.

In some versions, tip (400) is constructed from a non-magnetic metal, such as titanium. During fabrication, a solid piece of titanium is milled and/or turned to create the general shape as shown in FIGS. 8 and 9. After milling and/or turning, the shaped titanium piece is drilled to hollow-out tip (400) by drilling along the longitudinal axis of tip (400). For example, drilling creates open end (416) of collar (405) and void space (424) extending from open end (416) through flange portion (418), through shaft (402), and into conical protrusion (404). Based on the teachings herein, other ways to fabricate tip (400) and other materials suitable for tip (400) will be apparent to those of ordinary skill in the art.

In some versions, body (300) is constructed from a plastic by an injection molding process. Suitable plastics may include polyether-etherketone (PEEK), duroplastic, and/or other thermoplastics or thermosetting plastics, all or any of which may include glass-fiber and/or carbon-fiber reinforcement. Moreover, in some versions, body (300) and tip (400) are securely joined via the injection molding process. For example, tip (400) is positioned within the injection mold as an insert, and body (300) is molded around and within tip (400). Where such a process is used, the molten plastic flows into void space (424) of tip (400) via open end (416) of collar (405). The molten plastic fills void space (424) within tip (400) and also surrounds shaft (402) and collar (405). The molten plastic further fills the space (426) of collar (405) between fins (420, 422). The shape of the mold is such that the molten plastic continues to form body (300) in the shape as shown in FIGS. 1-2.

Figure 7:
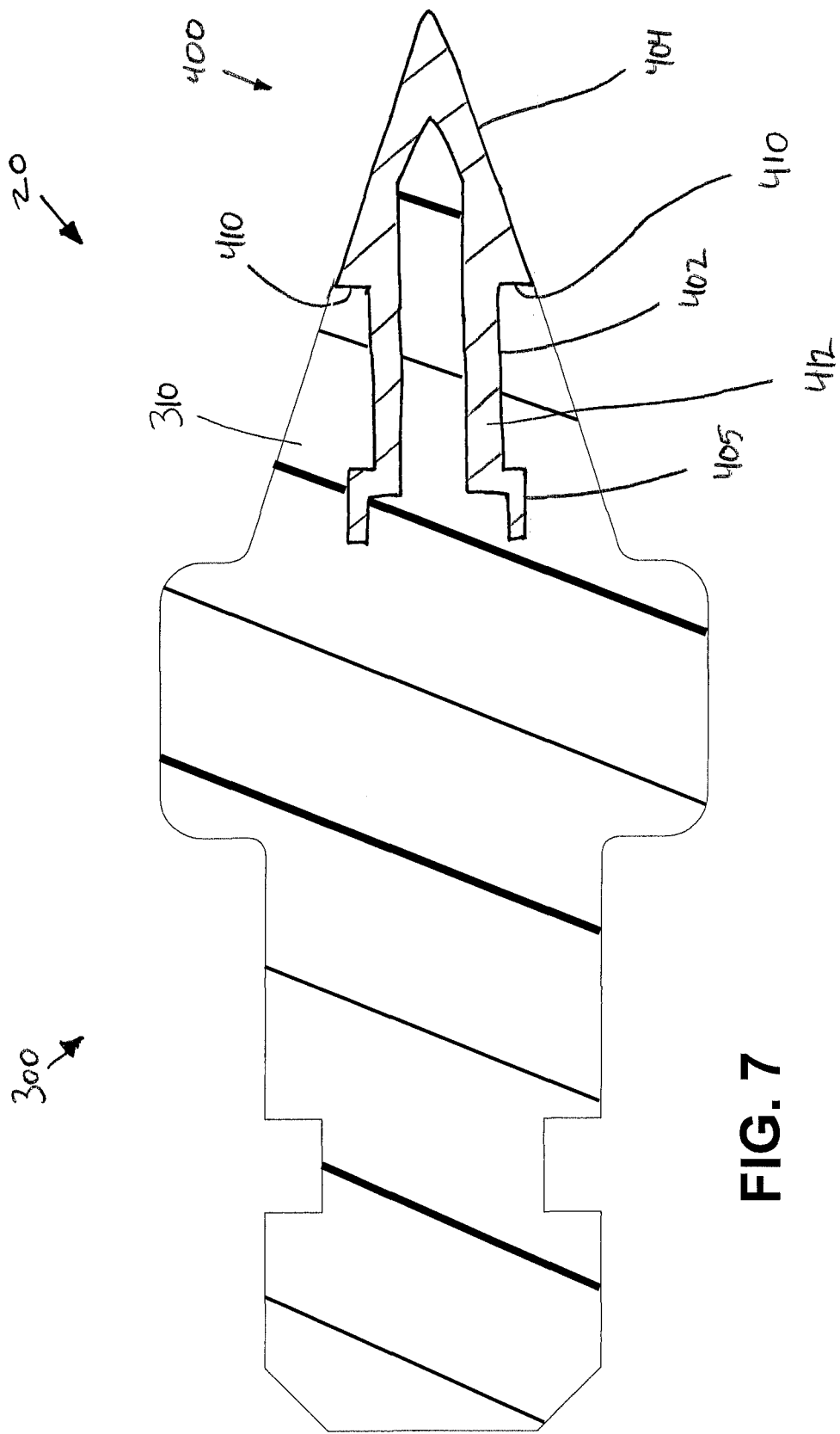
FIG. 7 depicts a cross section view of another exemplary cranial stabilization pin, taken along a line similar to that of the cross section view of FIG. 3 but for another exemplary pin that is not shown in perspective and side views but would otherwise be identical to the perspective and side views of FIGS. 1 and 2.
Figure 10:
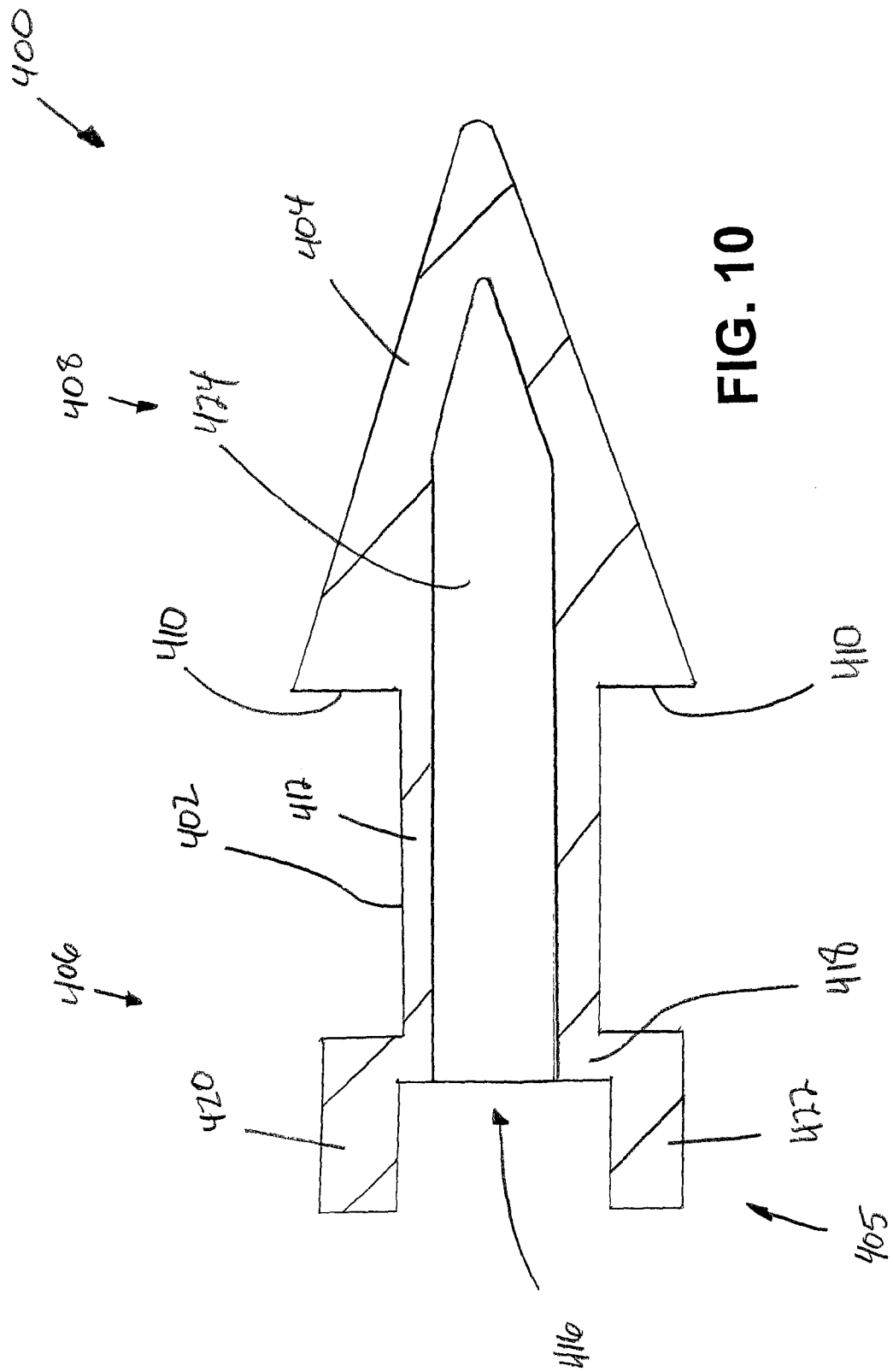
FIG. 10 depicts a cross section view of the tip of FIG. 9, taken along line 10-10 of FIG. 9.

Referring to FIGS. 7 and 10, cross sections of pin (20) and tip (400) show that final pin (20), in a molded design, has the plastic of body (100) encompassing void space (424) of tip (400) and surrounding shaft (402) and collar (405) of tip (400). Also, lip (410) of tip (400) abuts conical protrusion (310) of body (300) to provide a smooth transition from tip (400) to body (300). Using such a design and fabrication process, pin (20) is safe for use with and compatible with MR imaging, and is substantially radiolucent with a strong tip (400) having low mass such that only a minimal artifact is seen in the output of an imaging scan. Furthermore, using such a design and fabrication process, tip (400) and body (300) are securely joined such that pin (20) can withstand the torque and axial forces typical in a skull stabilization procedure using a skull clamp or other device. For instance, molding body (300) to tip (400) by molding plastic not only around the exterior surface of a portion of a low mass tip (400), but also within and through portions of tip (400) provides as strong and secure connection between body (300) and tip (400), suitable for withstanding torque and axial forces experienced in use.

While body (300) has been described as being constructed of plastic, and by an injection molding process, other suitable materials of construction and processes by which to construct body (300) will be apparent to those of ordinary skill in the art in view of the teachings herein. For example, body (300) may be fabricated by machining by turning, milling, etc. instead of injection molding. Additionally, other ways to securely join tip (400) and body (300) will be apparent to those of ordinary skill in the art in view of the teachings herein. For example, tip (400) and body (300) may be securely joined with an adhesive.

Figure 12:
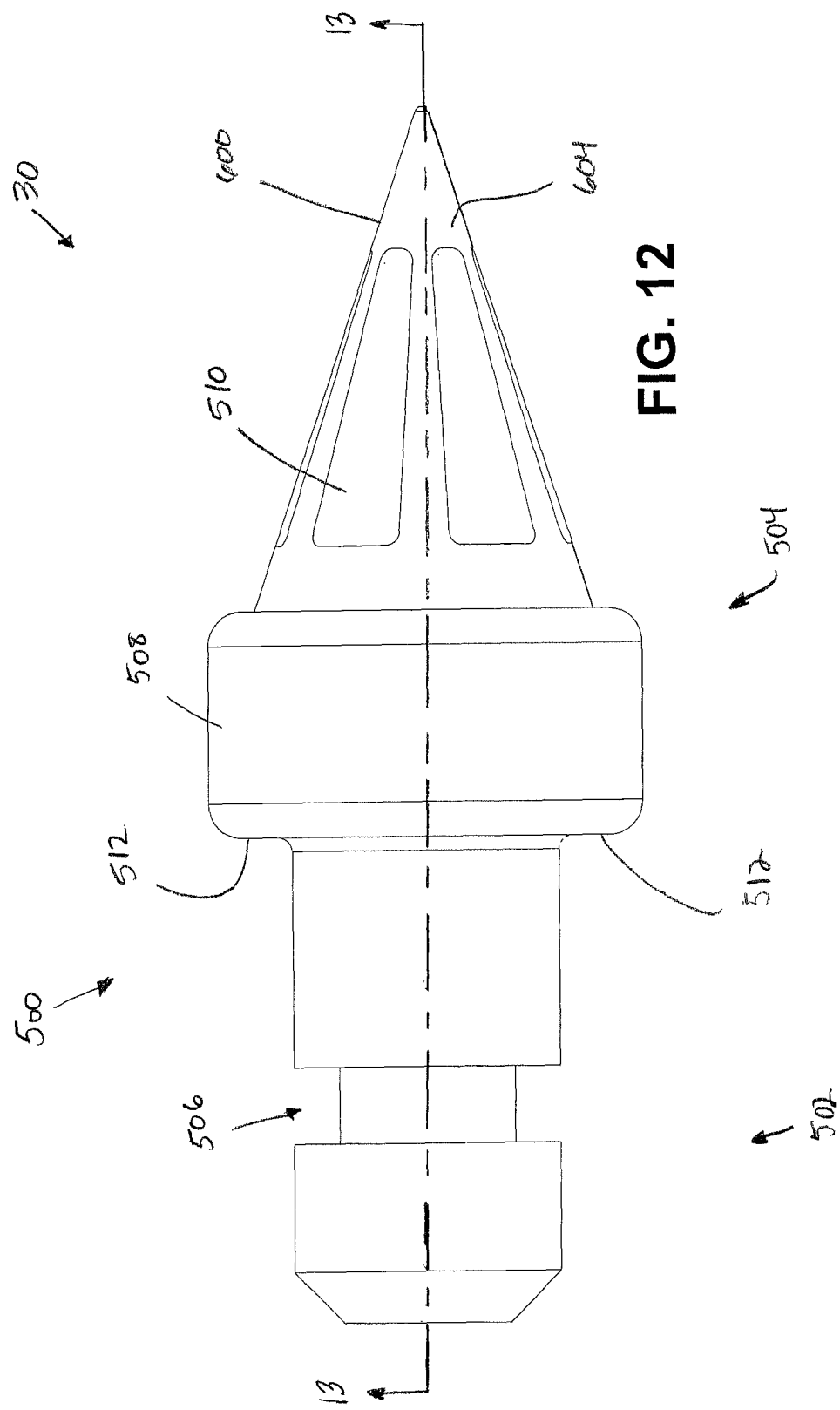
FIG. 12 depicts a side view of the pin of FIG. 11.
Figure 13:
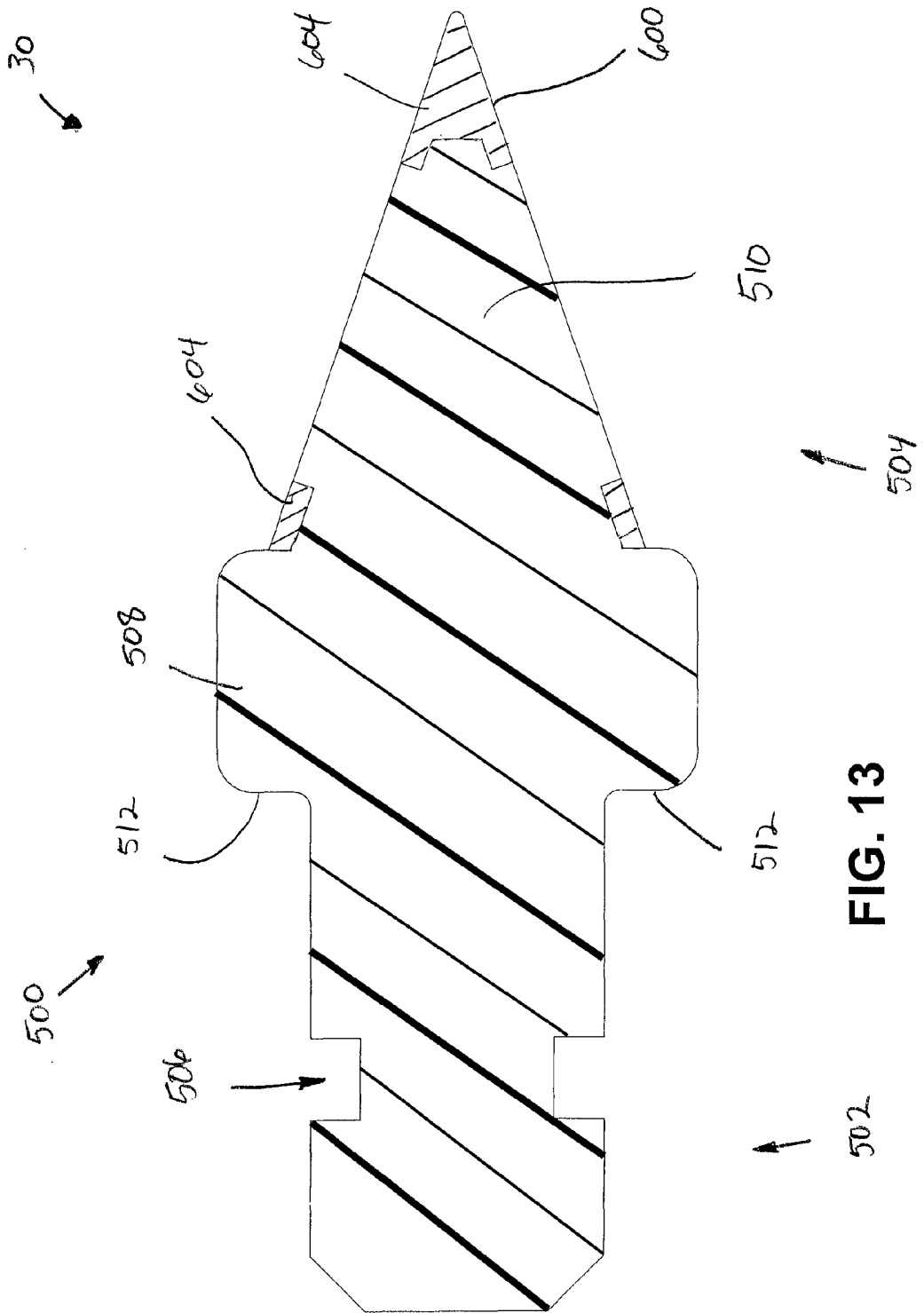
FIG. 13 depicts a cross section view of the pin of FIG. 12, taken along line 13-13 of FIG. 12.
Figure 14:
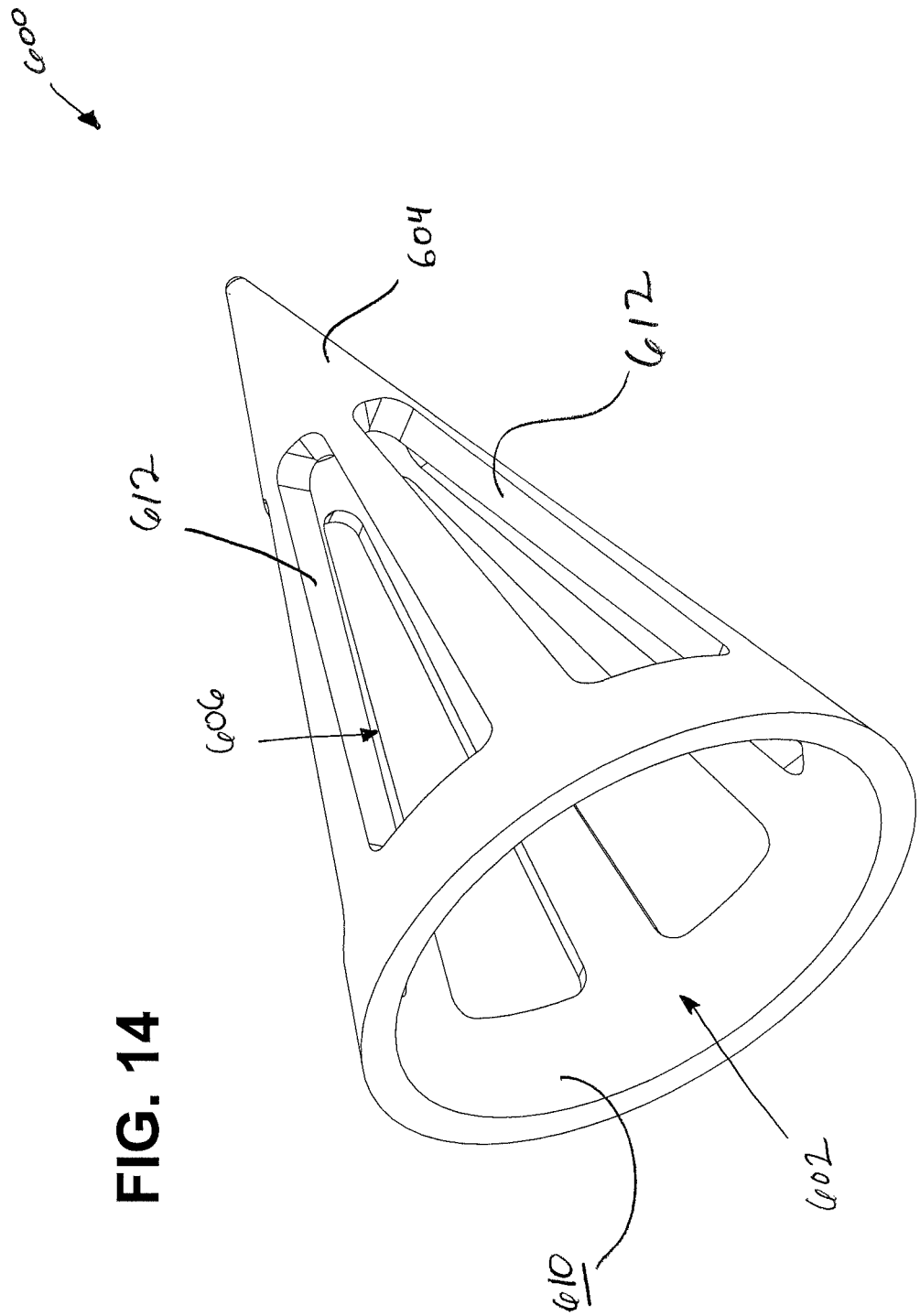
FIG. 14 depicts a perspective view of the tip of the pin of FIG. 11.
Figure 15:
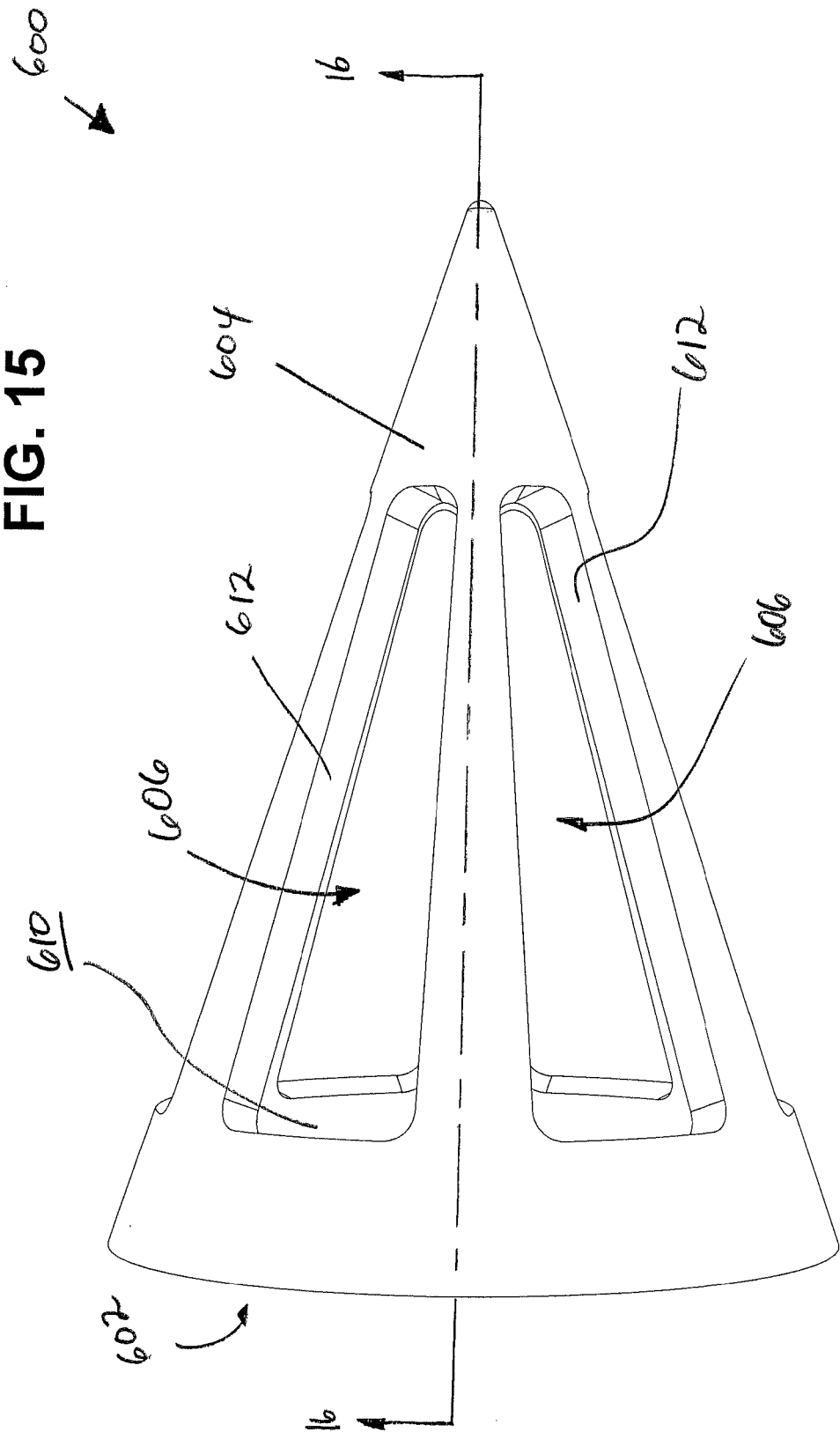
FIG. 15 depicts a side view of the tip of FIG. 14.
Figure 16:
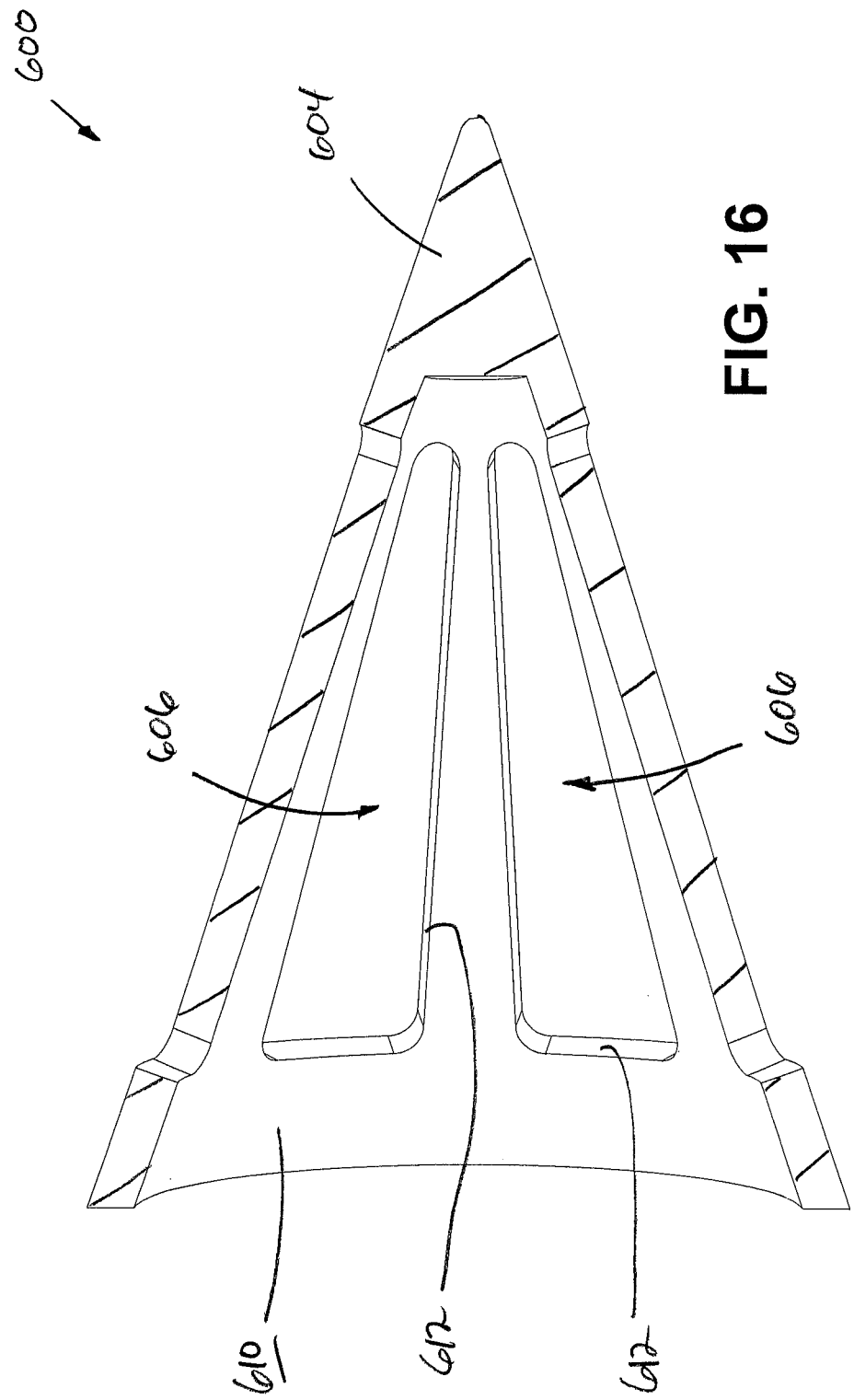
FIG. 16 depicts a cross section view of the tip of FIG. 15, taken along line 16-16 of FIG. 15.
Figure 17:
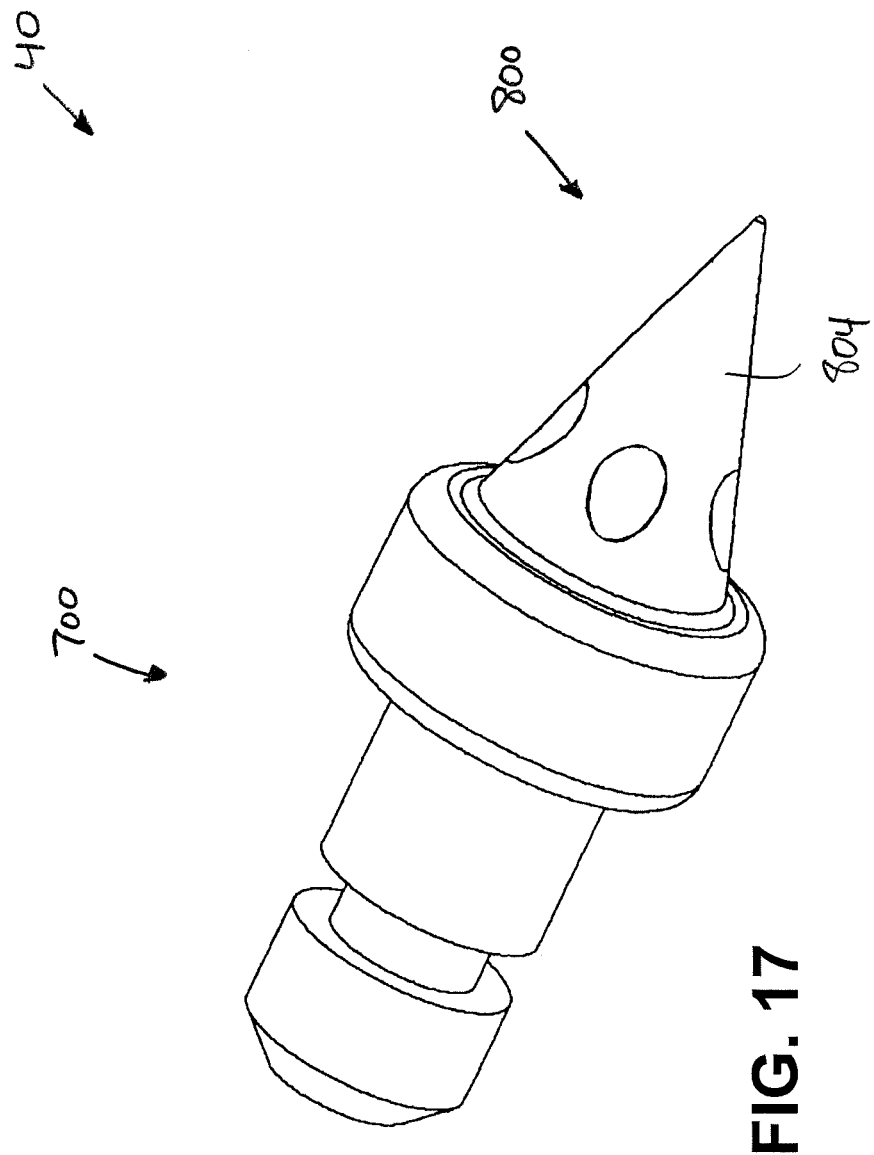
FIG. 17 depicts a perspective view of another exemplary cranial stabilization pin.
Figure 18:
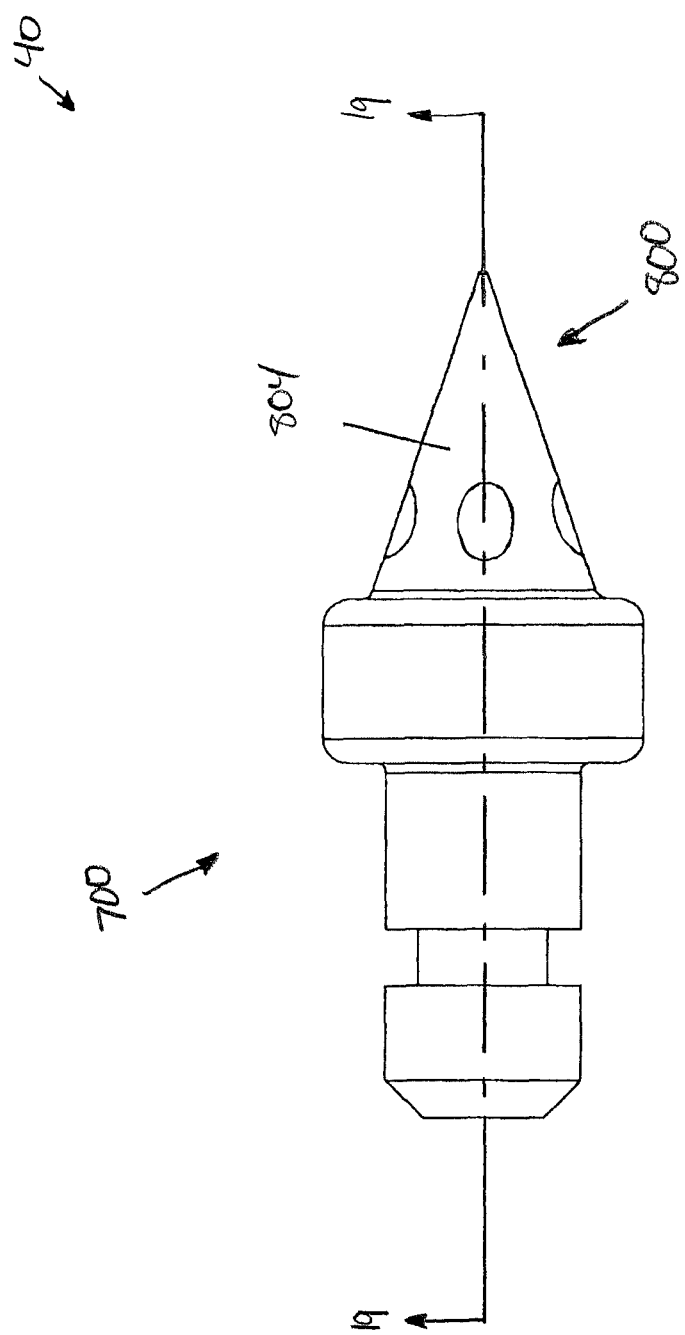
FIG. 18 depicts a side view of the pin of FIG. 17.
Figure 19:
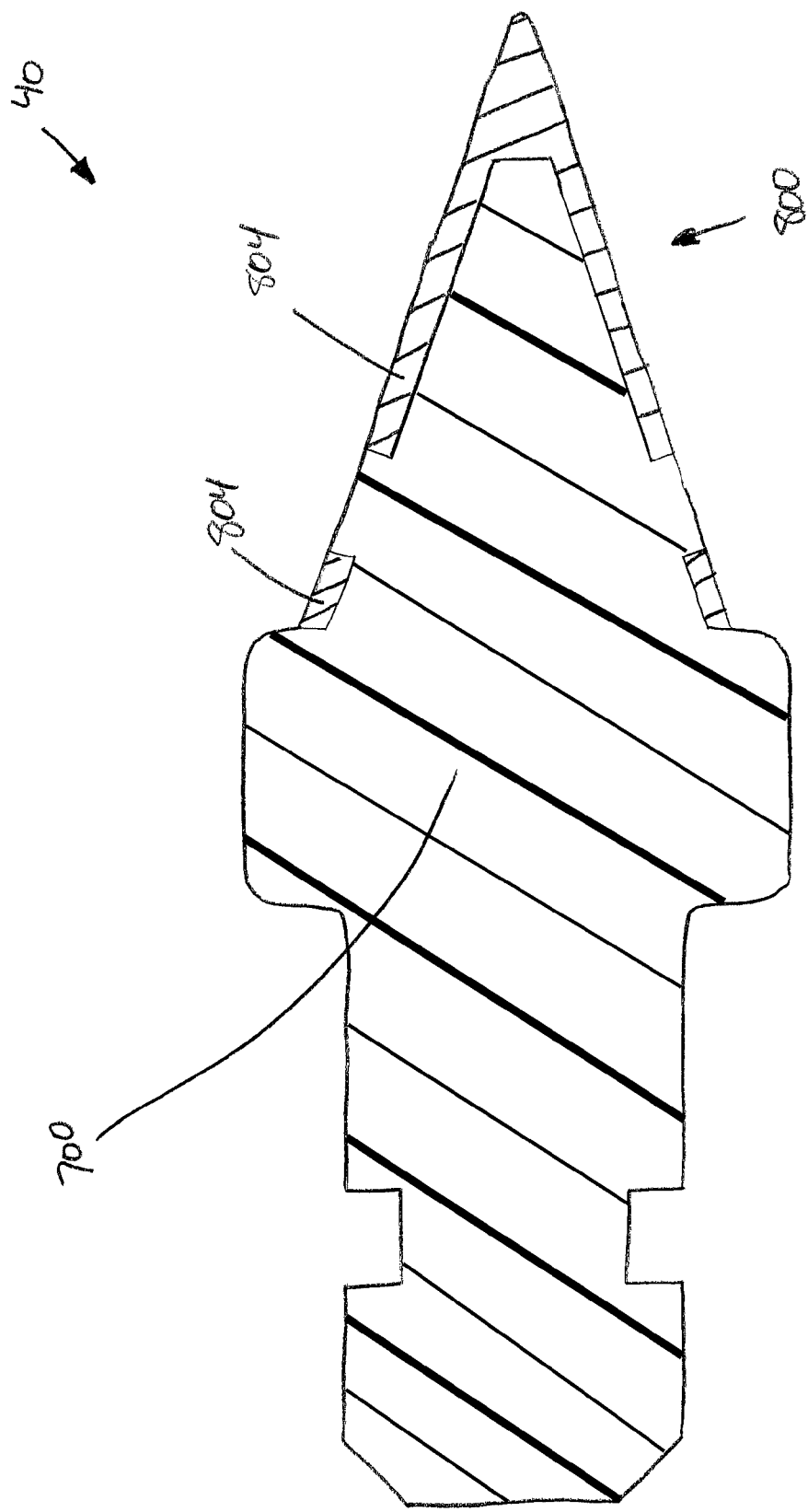
FIG. 19 depicts a cross section view of the pin of FIG. 18, taken along line 19-19 of FIG. 18.
Figure 20:
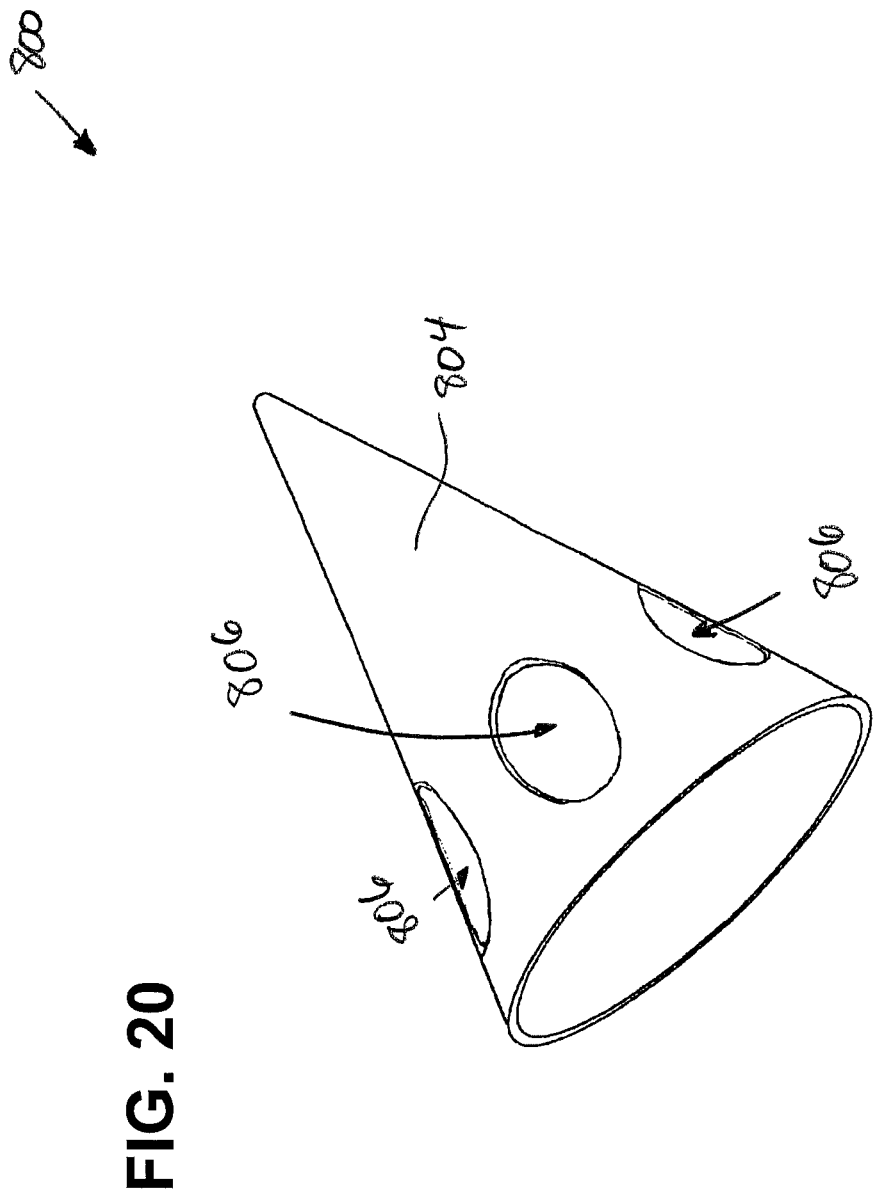
FIG. 20 depicts a perspective view of the tip of the pin of FIG. 17.
Figure 21:
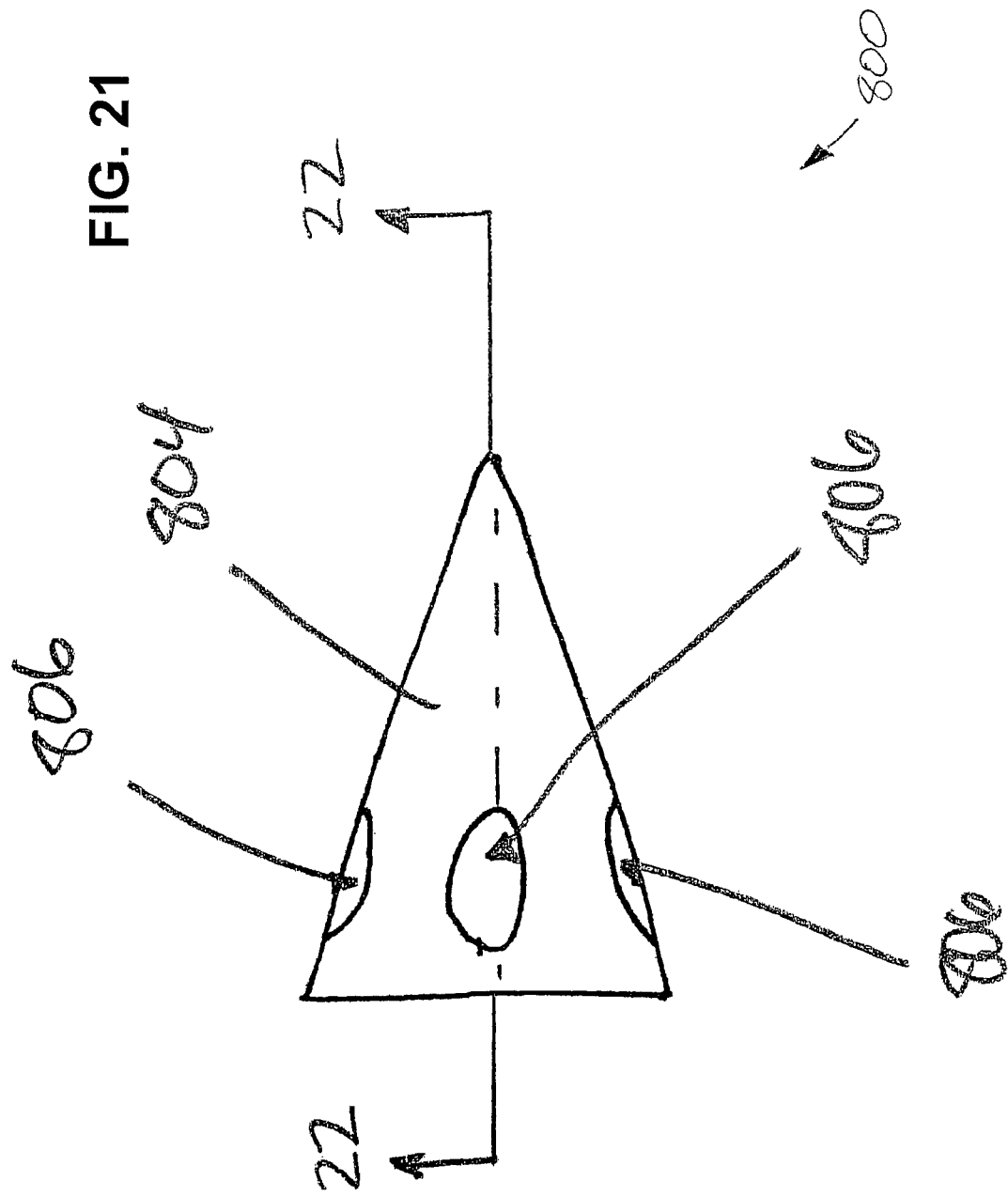
FIG. 21 depicts a side view of the tip of FIG. 20.
Figure 22:
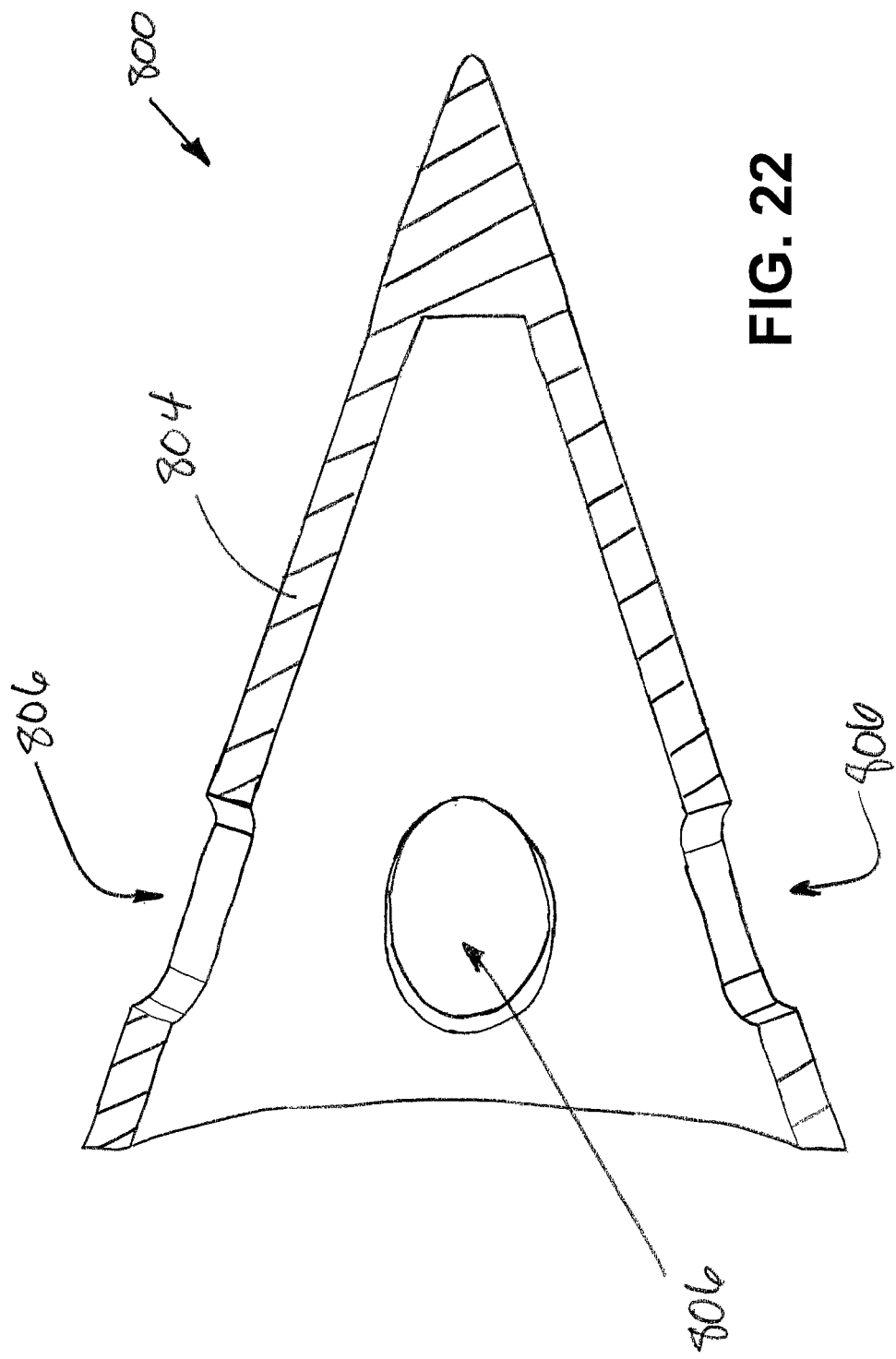
FIG. 22 depicts a cross section view of the tip of FIG. 21, taken along the line 22-22 of FIG. 21.

Referring now to FIGS. 11-16, another exemplary version of a skull pin (30) is shown. Skull pin (30) comprises body (500) and tip (600). Tip (600) is constructed from a non-ferrous, non-magnetic, biocompatible, and suitably strong material. By way of example, and not limitation, a suitable material for tip (600) is titanium. As shown in FIGS. 14-16, tip (600) comprises a cone-shape having inner cavity (602), sidewall (604), and at least one opening (606) in sidewall (604). Sidewall (604) has a thickness that is sufficient to provide the necessary strength during use to avoid failure of pin (30), while limiting the mass of tip (600) such that only minimal artifacts appear in the output of an imaging scan. By way of example only, and not limitation, in some versions the thickness of sidewall (604) is in the range of 0.1 mm to 1 mm. Those of ordinary skill in the art will understand that the thickness of sidewall (604) may be altered in some versions based on the application, imagining technique, and/or other strength influencing factors, e.g. the size and orientation of openings (606) in sidewall (604).

Openings (606) of sidewall (604) provide surface area for bonding tip (600) to body (500) while reducing the mass of tip (600). As mentioned above, the reduction in mass of tip (600) minimizes the appearance of artifacts in the output of imaging scans when pin (30) is used with various imaging technologies. Openings (606) have a triangular shape as shown in FIGS. 14-16. However, other shapes for openings (606) may be suitable as well. For instance, FIGS. 17-22 depict another version of a pin, pin (40), having tip (800) with openings (806) that have an oval shape. Still other shapes for openings (606) may include holes, longitudinal slats, latitudinal slats, diagonal slats, squares, or a combination of shapes. Based on the teachings herein, other suitable shapes for openings (606) will be apparent to those of ordinary skill in the art.

Tip (600) may be manufactured in a variety of ways. For example, fabricating tip (600) may involve metal production processes including casting, forging, flow forming, rolling, extrusion, sintering, metalworking, machining, milling, turning, bending, folding, or combinations of the above. Tip (600) may comprise a single piece or be made from a plurality of pieces securely joined together. In some versions, a single piece of material is folded and the ends of the piece joined together to form tip (600). Where a joining process is used in manufacturing tip (600), the joining processes may include welding, brazing, soldering, or combinations thereof. Still in other versions, a single piece of material is drilled to create inner cavity (602) of tip (600). Tip (600) is then milled and/or turned to create the outer cone or pointed shape. Sidewall (604) of tip (600) is then drilled or cut to create openings (606).

Figure 11:
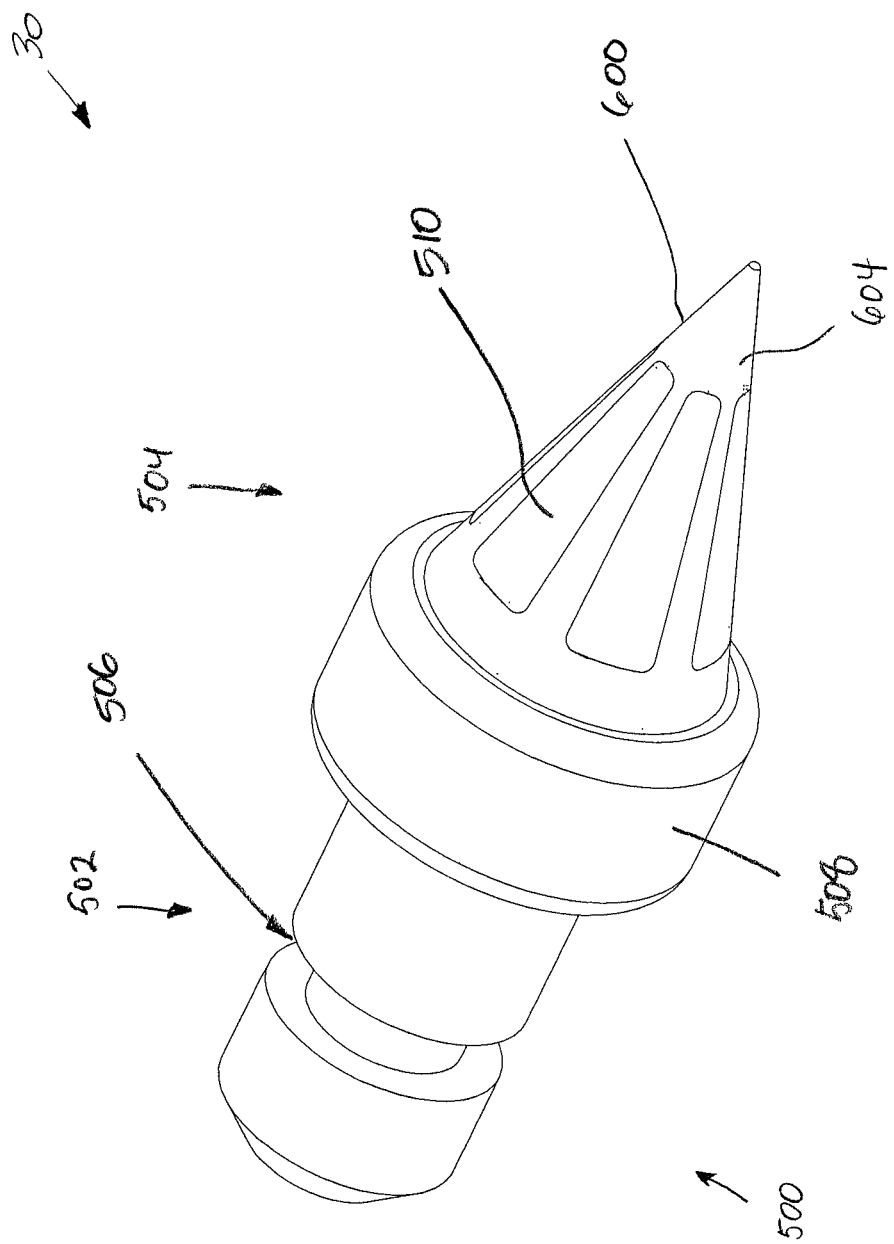
FIG. 11 depicts a perspective view of another exemplary cranial stabilization pin.

FIGS. 11-13 show tip (600) associated with body (500) of pin (30). Body (500) is constructed from a biocompatible radiolucent material that is safe for use with and compatible with MR imaging. Body (500) also has suitable strength and durability for use in a cranial stabilization application. Such a material may be non-ferrous and non-magnetic. Such a material may also be of low density, but with sufficient rigidity and resiliency for use in a cranial stabilization procedure. For instance, in some versions body (500) is comprised of polyether-etherketone (PEEK). Still in other versions, body (500) is comprised of other suitable thermoplastics or thermosetting plastics, which may include glass-fiber and/or carbon-fiber reinforcement. Still yet in other versions body (500) is comprised of duroplastic. Of course other suitable biocompatible radiolucent materials that are safe for use with and compatible with MR imaging may be used for body (500) of pin (30) and will be apparent to those of ordinary skill in the art in view of the teachings herein.

Body (500) comprises proximal end (502) and distal end (504). Distal end (504) is associated with tip (600) of pin (30). Proximal end (502) is associated with other cranial stabilization components. Body (500) is generally comparable to body (100) and body (300) described above. For example, body (500) incorporates annular recess (506), annular collar (508), and first surface (512) of annular collar (508) as described above with reference to body (100) and body (300). A difference between body (500) and the bodies (100, 300) described previously is that conical protrusion (510) of body (500) takes on a different shape to securely fit with tip (600) as will be described further below.

Referring now to the association of tip (600) to body (500), in some versions, body (500) and tip (600) are associated using an injection molding process. In some such versions, body (500) is formed entirely by injection molding while tip (600) is an insert to the injection mold. When molding occurs, the molded material bonds to tip (600) to produce a unitary structure. During the injection molding process, the molten material, e.g. plastic, fills inner cavity (602) of tip (600), bonding with interior surface (610) of inner cavity (602) as well as with the surface areas provided by edges (612) of openings (606) in sidewall (604) of tip (600). In such versions, sidewall (604) of tip (600) remains exposed.

In some versions, tip (600) may incorporate other features, alternatively or in addition to openings (606), to enhance bonding of tip (600) to body (500). For example, interior surface (610) of tip (600) may be configured with grooves or threads to increase the bonded surface area between body (500) and tip (600). Still in other versions, the injection molding material may encapsulate tip (600) so the final appearance of pin (30) is a single injection molded piece, although pin (30) comprises dual components of tip (600) and body (500). In such versions, the injection molding material will also bond with the outer surface, or sidewall (604), of tip (600), thereby increasing the bonded surface area. Based on the teachings herein, other techniques and features to incorporate to produce a pin having a tip that can withstand the torque and axial forces typical with a cranial stabilization procedure while having a low mass tip such that artifacts are minimal in imaging scan outputs will be apparent to those of ordinary skill in the art.

As mentioned above, another exemplary version for a skull pin, pin (40), is shown in FIGS. 17-22. Pin (40) may comprise body (700) and tip (800). The foregoing description regarding FIGS. 11-16 and pin (30) also describe pin (40), with the difference being that the shape of openings (806) in sidewall (804) of tip (800) are oval instead of triangular as with tip (600). Therefore, it shall be understood that the above description regarding pin (30) applies equally to pin (40) with the noted exception regarding the tip opening shape.

Figure 23:
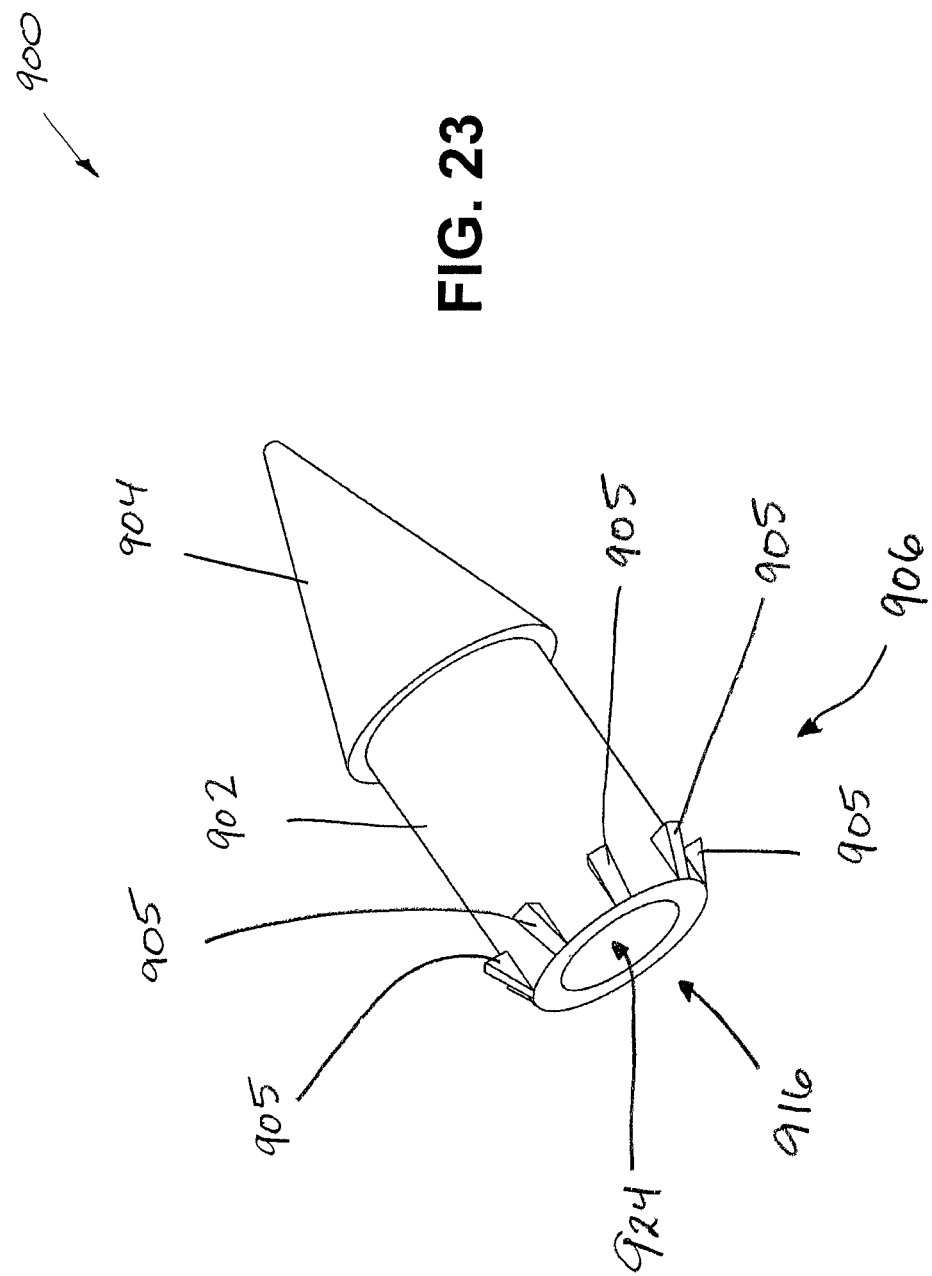
FIG. 23 depicts a perspective view of another exemplary tip for use in a cranial stabilization pin.

Referring now to FIG. 23, another exemplary tip (900) is shown. Tip (900) is configured for use with a body as described previously. Tip (900) comprises shaft (902), conical protrusion (904), and barb anchors (905). In the present example, shaft (902) comprises opening (916) at proximal end (906). Opening (916) provides access to void space (924) within shaft (902). In some versions void space (924) extends through shaft (902) and within conical protrusion (904). As shown in FIG. 23, shaft (902) comprises barb anchors (905) around proximal end (906). Barb anchors (905) provide additional surface area for bonding tip (900) to an exemplary body similar to those described previously. Barb anchors (900) provide a secure connection of tip (900) to a body such that the resultant pin is suitable to withstand the torque and axial forces common in a cranial stabilization procedure.

Figure 24:
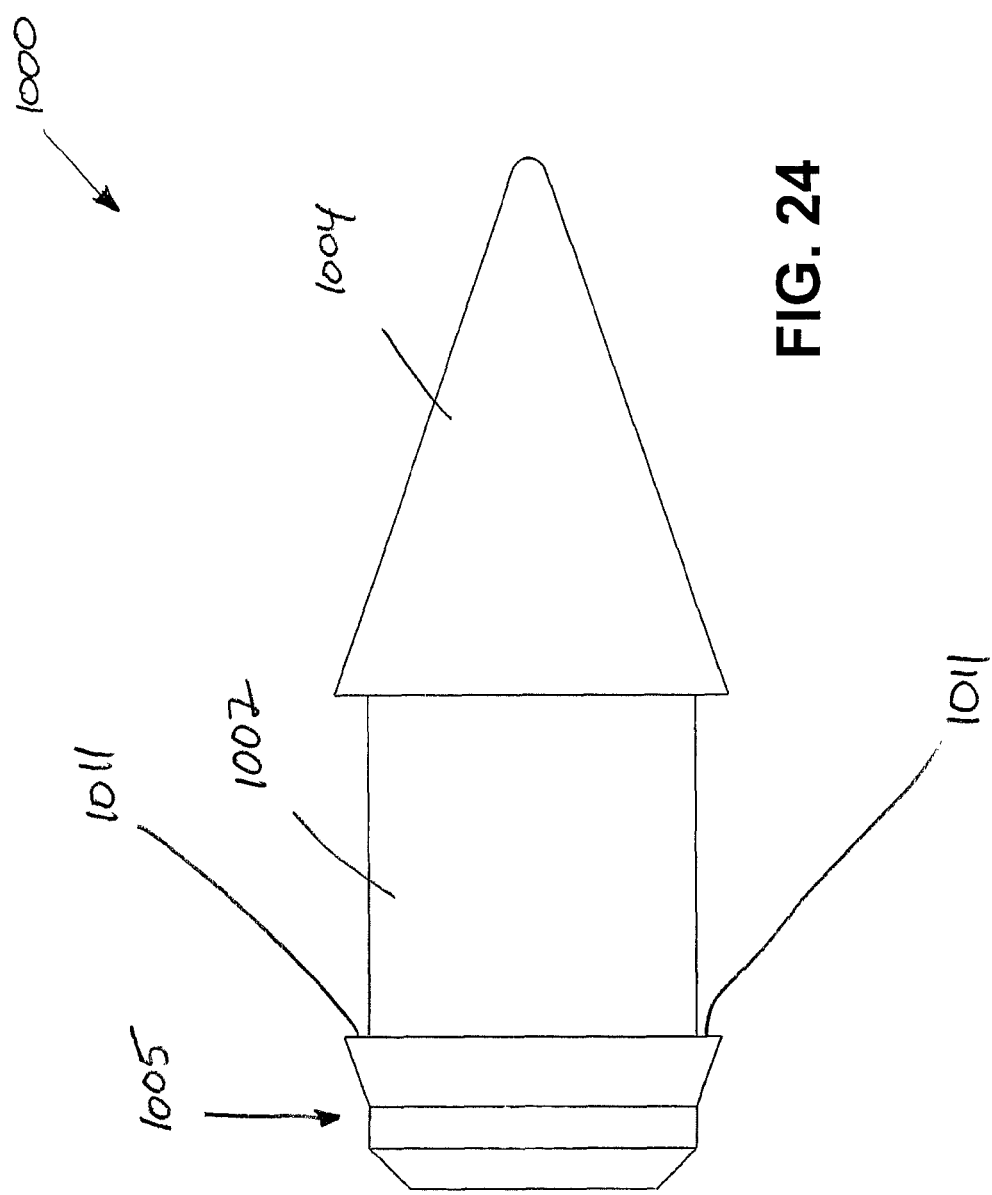
FIG. 24 depicts a side view of another exemplary tip for use in a cranial stabilization pin.

Referring now to FIG. 24, another exemplary tip (1000) is shown. Tip (1000) is configured for use with a body as described previously. Tip (1000) comprises conical protrusion (1004), shaft (1002), and collar (1005). In the present example, tip (1000) is substantially hollow to reduce its mass to reduce artifacts in imaging scans as discussed previously. Of course tip may be substantially or completely solid in other examples. Collar (1005) comprises lip (1011) that extends around the perimeter of collar (1005) and has a larger diameter than shaft (1002) such that lip (1011) overhangs shaft (1002). Lip (1011) provides additional surface area for bonding tip (1000) to a body. Lip (1011) provides a secure connection of tip (1000) to a body such that the resultant pin is suitable to withstand the torque and axial forces common in a cranial stabilization procedure.

Figure 25:
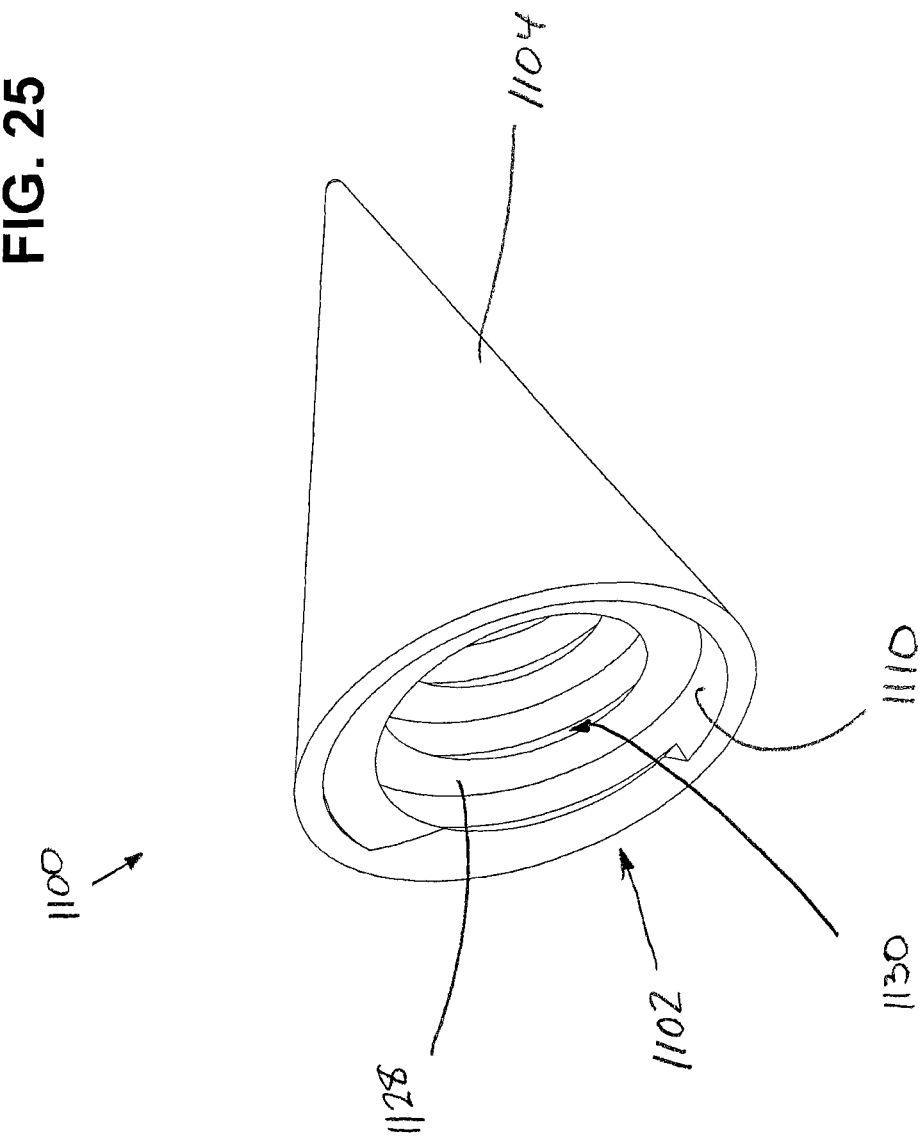
FIG. 25 depicts a perspective view of another exemplary tip for use in a cranial stabilization pin.
Figure 26:
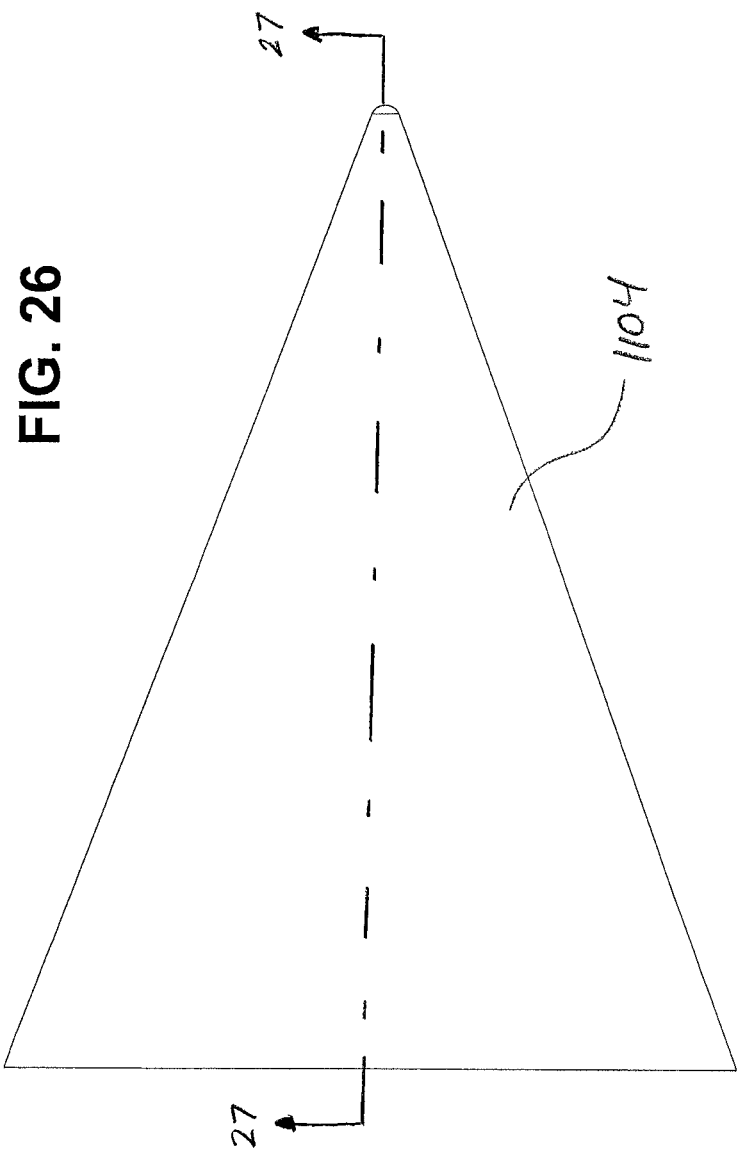
FIG. 26 depicts a side view of the tip of FIG. 25.
Figure 27:
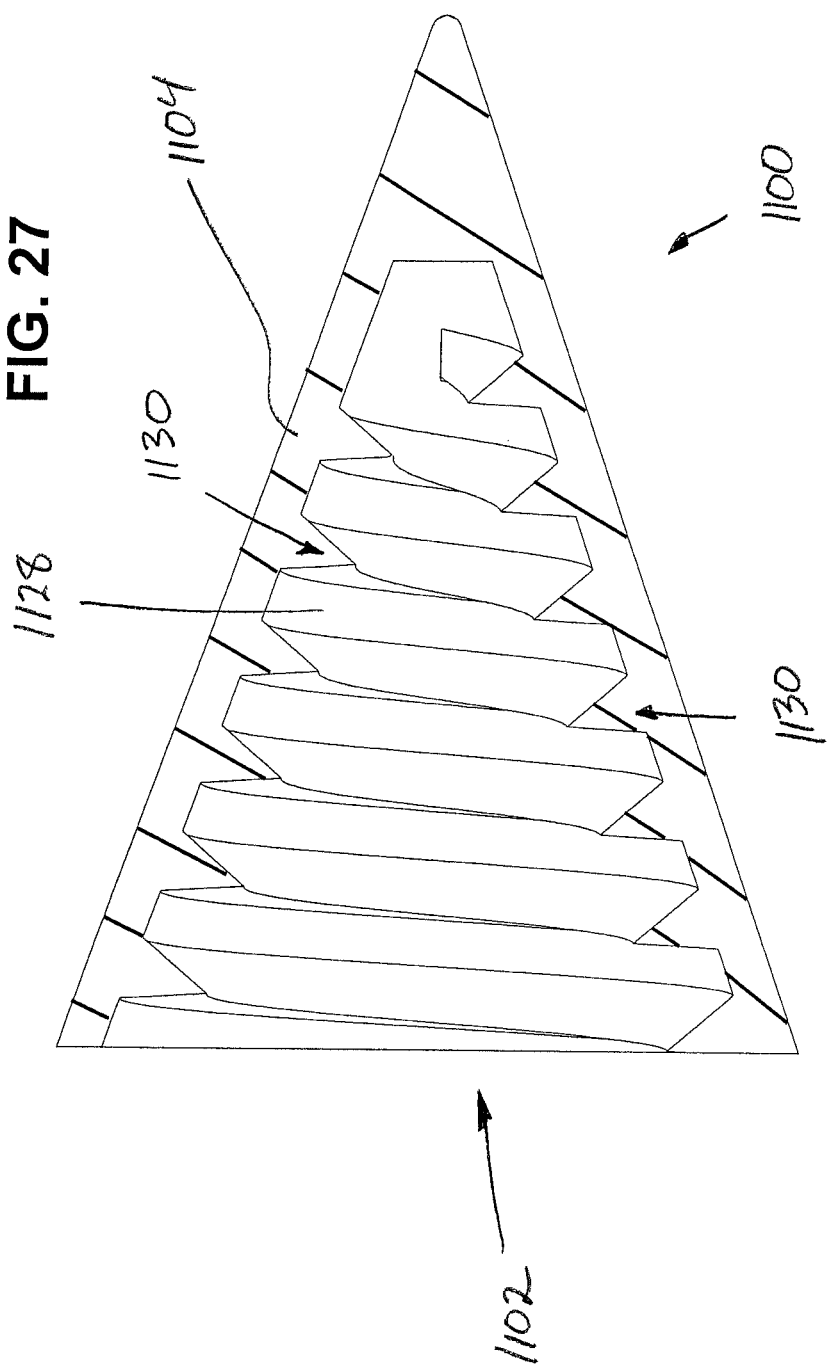
FIG. 27 depicts a cross section view of the tip of FIG. 25, taken along the line 27-27 of FIG. 26.

Referring now to FIGS. 25-27, another exemplary tip (1100) is shown. Tip (1100) comprises inner cavity (1102), sidewall (1104), and interior surface (1110). As shown, sidewall (1104) does not include openings similar to tips (600, 800), of course such openings may be added. Interior surface (1110) of tip (1100) comprises ridges (1128) that extend from one end of tip (1100) to the other end. Ridges (1128) further define gaps (1130). As shown in the present example depicted in FIGS. 25 and 27, ridge (1128) is a continuous spiral-shaped member extending along the interior of tip (1100). Of course multiple discontinuous ridges (1128) with other orientations may be used in other versions, e.g. multiple ridges extending longitudinally within tip (1100) from the open end to the pointed end. Furthermore, based on the teachings herein, those of ordinary skill in the art will understand that other protruding shapes or recesses may be used within the interior of tip (1100) instead of, or in addition to, ridges (1128). In the present example, tip (1100) is secured to a body, e.g. similar to body (500) or body (700), by injection molding, of course other methods of securing tip (1100) to a body may be used, e.g. chemically bonding with an adhesive or mechanical fastening. With injection molding, ridges (1128) provide increased surface area within the interior of tip (1100) for bonding between the body and tip (1100). With such a design, tip (1100) has a sufficient low mass to produce only a minimal artifact in the output of an imaging scan while also having the integrity to withstand the torque and axial forces typical in a skull stabilization procedure. The materials of construction and method of making tip (1100) and the body may be the same or similar to those described for other exemplary pins.

Figure 28:
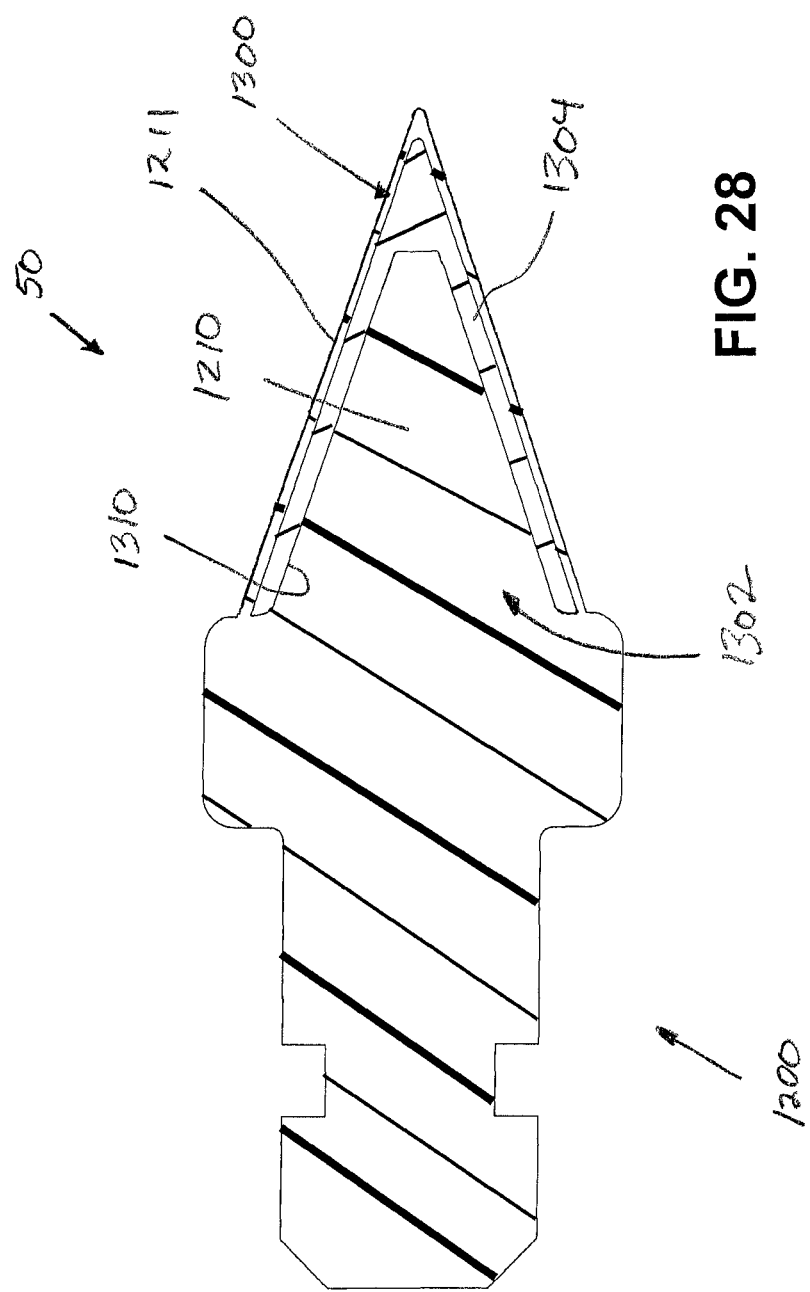
FIG. 28 depicts a cross section view of another exemplary cranial stabilization pin with the tip encased within the body.

Referring now to FIG. 28, another exemplary cranial stabilization pin (50) is shown that incorporates an encased tip. In the present example, pin (50) comprises body (1200) and tip (1300). Tip (1300) is overmolded by body (1200) such that all or substantially all of tip (1300) is surrounded by body (1200). Of course less than substantially all of tip (1300) may be overmolded in some versions such that a distal portion of tip (1300) is visible. In the present example, tip (1300) is similar to the tip shown in FIG. 26, although without internal ridges. Of course, tip (1300) could also be identical to tip (1100) of FIGS. 25-27 in other examples. Furthermore, any of the tips described herein could be adapted for use in a design overmolding the tip with the body. As shown in FIG. 28, tip (1300) comprises interior surface (1310) and internal cavity (1302) that is filled by inner conical protrusion (1210) of body (1200). Sidewall (1304) of tip is surrounded by outer conical sheath (1211) of body (1200) such that tip (1300) is encased within body (1200). In the present example, tip (1300) and body (1200) are secured together by injection molding, where both interior surface (1310) and sidewall (1304) of tip (1300) provide surface area for bonding with conical protrusion (1210) and outer conical sheath (1211) of body (1200). Of course other methods of securing tip (1300) to body (1200) may be used, e.g. chemically bonding with an adhesive or mechanical fastening. In use, tip (1300) of pin (50) has a sufficient low mass to produce only a minimal artifact in the output of an imaging scan while pin (50) also has the integrity to withstand the torque and axial forces typical in a skull stabilization procedure. The materials of construction and method of making pin (50) may be the same or similar to those described for other exemplary pins.

While above exemplary pins have been described as having a molded body bonded to a tip, other connection methods for securing a tip to a body will be apparent to those of ordinary skill in the art in view of the teachings herein. For example, body could be molded separately from tip and tip may be secured to body with a suitable fastener. In some versions, tip may snap-fit to body. In other versions tip may be screwed to body. Still in some other versions tip may be glued or chemically adhered to body. Also, any of the bodies described may be constructed by machining, e.g. milling, turning, etc., instead of or in addition to molding.

Based on the teachings herein, it will be appreciated by those of ordinary skill in the art that in any of the described examples, and examples not explicitly described but within the scope of the claims, the sizes and proportions of the tip and body may be altered. For example, the tip may be sized such that the portion of the tip extending from the body is small such that the output of an imaging scan shows a minimal artifact. Furthermore, the tip may be sized such that the portion of the tip extending from the body is generally equivalent to the portion of the tip that would penetrate the patient's skull during a stabilization procedure. In such an example, the exposed portion of the tip when not in use would be covered by bone when in use. With such a design, artifacts in the output of imaging scans may be minimized with the tip not exposed when in use.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of whatever claims recite the invention, and is understood not to be limited to the details of structure and operation shown and described in the description.

What is claimed is:

1. A skull pin for use with a stabilizing device, wherein the pin comprises:
   a. a tip, wherein the tip is configured to contact a patient's skull, wherein the tip comprises a conical member, wherein the conical member comprises:
      i. a point at a distal end of the tip, wherein the point is configured to contact the patient's skull,
      ii. a substantially thin sidewall, wherein the substantially thin sidewall comprises an exterior surface and an interior surface, wherein the interior surface defines an inner cavity of the tip,
      iii. one or more protrusions formed in the interior surface of the sidewall; and
   b. a molded body, wherein the molded body comprises;
      i. a proximal end dimensioned to fit in an opening of a skull clamp arm, and
      ii. a distal end secured to and extending within the inner cavity of the tip and contacting the one or more protrusions, wherein the tip is an insert piece bonded to the molded body during molding to form a unitary structure for the skull pin where the tip is non-removable from the molded body.

2. The pin of claim 1, wherein the one or more protrusions comprise one or more ridges, wherein the one or more ridges define one or more gaps between the ridges, wherein the distal end of the body extends within the inner cavity of the tip and fills the one or more gaps defined by the ridges.

3. The pin of claim 1, wherein the one or more protrusions comprise a threaded configuration.

4. The device of claim 1, wherein the conical portion of the tip is substantially hollow.

5. The pin of claim 1, wherein the device is substantially radiolucent.

6. The pin of claim 1, wherein the tip is comprised of titanium and the body is comprised of plastic.

7. A skull pin for use with a stabilizing device, wherein the pin comprises:
   a. a tip, wherein the tip is configured to contact a patient's skull, wherein the tip comprises:
      i. a conical portion,
      ii. a point at a distal end of the conical potion, wherein the point is configured to contact the patient's skull,
      iii. a substantially thin sidewall, wherein the substantially thin sidewall comprises an exterior surface and an interior surface, wherein the interior surface defines an inner cavity of the tip,
      iii. one or more protrusions formed in the sidewall of the tip, wherein the one or more protrusions define a distally-decreasing interior diameter of the inner cavity of the tip; and
   b. a body, wherein the body comprises a proximal end and a distal end, wherein the proximal end of the body is configured to be selectively retained within a skull clamp, wherein the distal end of the body is secured to the tip, wherein the distal end of the body extends within the inner cavity of the tip and contacts the one or more protrusions.

* * * * *